US006436673B1

(12) United States Patent
Worley et al.

(10) Patent No.: US 6,436,673 B1
(45) Date of Patent: Aug. 20, 2002

(54) POLYNUCLEOTIDES ENCODING A NOVEL NEURONAL CELL GROWTH FACTOR

(75) Inventors: Paul Worley; Cynthia Tsui, both of Baltimore, MD (US)

(73) Assignee: The Johns Hopkins University School of Medicine, Baltimore, MD (US)

( * ) Notice: Subject to any disclaimer, the term of this patent is extended or adjusted under 35 U.S.C. 154(b) by 0 days.

(21) Appl. No.: 09/098,358

(22) Filed: Jun. 16, 1998

Related U.S. Application Data

(62) Division of application No. 08/631,607, filed on Apr. 8, 1996, now Pat. No. 5,767,252.
(51) Int. Cl.[7] ......................... C12N 15/18; C12N 15/63; C12N 15/85
(52) U.S. Cl. .................. 435/69.4; 435/320.1; 435/325; 435/252.3; 536/23.51
(58) Field of Search ....................... 536/23.51; 435/325, 435/252.3, 320.1, 69.4

(56) References Cited

PUBLICATIONS

Hsu, Yung–Chih et al., "Human Neuronal Pentraxin II (NPTX2): Conservation, Genomic Structure and Chromosomal Localitzation", *Genomics* 28:220–227 (1995).
Reid et al., J. Biological Chemistry 269 (1994) 32615–32620.
Noland et al., J. Biological Chemistry 269 (1994) 32607–32614.
Rudinger In "Peptide Hormons" ed. J.A. Parsons, University Park Press, Baltimore, pp. 1–7 (Jun. 1976).
Tsui et al., "Narp, a novel member of the pentraxin family, promotes neurite outgrowth and is dynamically regulated by neuronal activity", *Jln of Neuroscience* (Apr. 15, 1996) 16(8): 2463–2478.
Tsui et al., "Narp, a novel member of the pentraxin family, promotes neurite outgrowth and is dynamically regulated by neuronal activity.", *Molecular Biology of the Cell* (11/1995) 6:214A.
Tsui et al., "Narp, a novel member of the pentraxin family of proteins that is synthesized, secreted and active as a monomeric molecule", *Society for Neuroscience Abstracts* (11/96) 22:299.
Goodman et al., "Long pentraxins: an emerging group of proteins with diverse functions", *Cytokine & Growth Factor Reviews* (1996) 7(2):191–202.
Omeis et al., "Mouse and human neuronal pentraxin 1 (NPTX1): conservation, genomic structure, and chromosomal location", *Genomics* (1996) 36:543–545.

*Primary Examiner*—Gary L. Kunz
*Assistant Examiner*—Robert C. Hayes
(74) *Attorney, Agent, or Firm*—Gray Cary Ware & Freidenrich LLP; Lisa A. Haile

(57) ABSTRACT

A novel neuronal cell growth factor, neuronal-activity regulated pentraxin, Narp, is provided, as well as polynucleotides encoding Narp. Narp is useful for induction of dendritic neurite outgrowth as well as promotion of neuronal migration. Methods for treatment of subjects having a neuronal cell disorder, utilizing Narp of the invention, are also provided.

7 Claims, 5 Drawing Sheets

```
Narp     MLALLTAGVA LAVAAGQAQD NPIPGSRFVC TALPPEAAPA GCPLPAMPMQ      50
Apexin   MLALLAAGVA FAVVV-LAQD KPLPGSHFVC SAIPPEALFA GCPLPATPMQ      49
NPTX2    MLALLAASVA LAVAAG-AQD SPAPGSRFVC TALPPEAVHA GCPLPAMPMQ      49

Narp     GGALSPEEEL RAAVLHWRET VVQQKETLGA QFEAIRELTS KLARCEGLAG      100
Apexin   GVSLSPEEEL RAAVLQLRET VVMQKETLGA QFEAIRELTS KLARCEGLMA       99
NPTX2    GGAQSPEEEL RAAVLQLRET VVQQKETLAS AF-AIRELTG KLARCEGLAG       98

Narp     GKARGTGATG KDTMGDLPRD PGHVVEQLSR SLQTLKDRLE SLELQLHTNA       150
Apexin   GKA----ESS KDTMGDLPRD PSRVVEQLSR SLQMLKDRLE SF--LELRTNA      143
NPTX2    GKARGAGATG KDTMGDLPRD PGHVVEQLSR SLQTLKDRLE SLEHQLRAINV      148

Narp     SNAGLPSDFR EVLQRRLGEL ERQLLRKVAE LEDEKSLLHN ETSAHRQKTE        200
Apexin   SNTTGLPSDFR EVLQRRLGEL ERQLLRKVAE LEDEKSLLHN ETSAHQQKTE       193
NPTX2    SNAGLPGDFR EVLQQRLGEL ERQLLRKVAE LEDEKSLLHN ETSAHRQKTE       198

Narp     NTLNALLQRV TELERGNSAF KSPDAFKVSL PLRTNYLYGK IKKTLPELYA        250
Apexin   NTLNALLQRV TELERGNSAF KSPDAFKVSL PFRTNYLYGK IKKTLPELYS        243
NPTX2    STLNALLQRV TELERGNSAF KSPDAFKVSL PLRTNYLYGK IKKTLPELYA       248

Narp     FTICLWLRSS ASPGIGTPFS YAVPGQANEI VLIEWGNNPI ELLINDKVAQ        300
Apexin   FTICLWLRSS ASPGIGTPFS YAVPGQANEI VLIEWGNNPI ELLINDKVAQ        293
NPTX2    FTICLWLRSS ASPGIGTPFS YAVPGQANEI LLIEWGNNPI ELLINDKVAQ       298

Narp     LPLFVSDGKW HHICITWTTR DGMWEAFQDG EKLGTGENLA PWHPIKPGGV        350
Apexin   LPLFVSDGKW HHICITWTTR DGLWEAFQDG EKLGTGENLA PWHPIKSGGV        343
NPTX2    LPLFVSDGKW HHICIVWTTR DGMWEAFQDG EKLGTGENLA PWHPIKPGGV       348

Narp     LILGQEQDTV GGRFDATQAF VGELSQFNIW DRVLRAGEII NIANCSTNMP        400
Apexin   LILGQEQDTV GGRFDATQAF VGELSQFNIW DRVLRPQEIS NIANCSLNMA        393
NPTX2    LILGQEQDTV GGRFDATQAF VGELSQFNIW DRVLRAQEIV NIANCSTNMP       398

Narp     GNIIPWVDNN VDVFGGASKW PVETCEERLL DL                          432
Apexin   GNIIPWVDNN VDVFGGASKW PVETCEERLL DL                          425
NPTX2    GNIIPWVDNN VDVFGGASKW PVETCEEALL DL                          430
```

FIG. 2B

POLYNUCLEOTIDES ENCODING A NOVEL NEURONAL CELL GROWTH FACTOR

This application is a divisional application of U.S. application Ser. No. 08/631,607, filed Apr. 8, 1996, now U.S. Pat. No. 5,767,252, issued Jun. 16, 1998.

STATEMENT AS TO FEDERALLY SPONSORED RESEARCH

This invention was made with government support by grant no. MH53608 from the National Institutes of Mental Health. The government has certain rights in this invention.

FIELD OF THE INVENTION

This invention relates generally to the field of neurobiology and more specifically to a novel neuronal cell growth factor, polynucleotides encoding the factor, and methods of use.

BACKGROUND OF THE INVENTION

The mature central nervous system exhibits the capacity to alter cellular interactions as a function of the activity of specific neuronal circuits. This capacity is believed to underlie learning and memory as well as aspects of postnatal development of the brain (Schatz, C., *Neuron*, 5:745, 1990). Cellular mechanisms underlying activity-dependent plasticity are known to be initiated by rapid, transmitter-induced changes in membrane conductance properties and activation of intracellular signaling pathways (Bliss and Collingridge, *Nature*, 361:31, 1993). Several lines of evidence also indicate a role for rapid synthesis of mRNA and protein in long-term neuroplasticity. For example, classical studies of learning and memory demonstrate a requirement for protein synthesis in a long-term, but not short-term memory (Flexner, ,et al., *Science*, 141:57, 1963; Agranoff, B., *Basic Neurochemistry, 3rd Edition*, 1981; Davis and Squire, *Physiol. Bull.*, 96:518, 1984), and long-term enhancement of synaptic connectivity, studied in cultured invertebrate neurons (Montarolo, et al., *Science*, 234:1249, 1986; Bailey, et al., *Neuron*, 9:749, 1992) or in the rodent hippocampus (Frey, et al., *Science*, 260:1661, 1993; Nguyen, et al., *Science*, 265:1104, 1994), is blocked by inhibitors of either RNA or protein synthesis. Importantly, inhibitors of macromolecular synthesis are most effective when administered during a brief time window surrounding the conditioning stimulus indicating a special requirement for molecules that are rapidly induced (Goelet, et al., *Nature*, 322:419, 1986).

Immediate early genes (IEGs) are rapidly induced in neurons by neurotransmitter stimulation and synaptic activity and are hypothesized to be part of the macromolecular response required for long-term plasticity (Goelet, et al., supra; Sheng and Greenberg, *Neuron*, 4:477, 1990; Silva and Giese, *Neurobiology*, 4:413, 1994). To identify cellular mechanisms that may contribute to long-term plasticity in the vertebrate brain, differential cloning techniques have been used to identify genes that are rapidly induced by depolarizing stimuli (Nedivi, et al., *Nature*, 363:713, 1993; Qian, et al., *Nature*, 361:453, 1993; Yamagata, et al., *Neuron*, 11:371, 1993; Yamagata, et al., *Learning and Memory* 1:140, 1994; Yamagata, et al., Journal of biological Chemistry, 269:16333, 1994; Andreasson and Worley, *Neuroscience*, 69:781, 1995; Lyford, et al., *Neuron*, 14:433, 1995). In contrast to the earlier focus on transcription factors, many of the newly characterized IEGs represent molecules that can directly modify the function of cells and include growth factors (Nedivi, et al., supra; Anreasson and Worley, supra), secreted enzymes that can modify the extracellular matrix, such as tissue plasminogen activator (Qian, et al., supra ), enzymes involved in intracellular signaling, such as prostaglandin synthase (Yamagata, et al., supra), and a novel homolog of H-Ras, termed Rheb (Yamagata, et al., supra), as well as a novel cytoskeleton-associated protein, termed Arc (Lyford, et al., supra). The remarkable functional diversity of this set of rapid response genes is representative of the repertoire of cellular mechanisms that are likely to contribute to activity-dependent neuronal plasticity.

SUMMARY OF THE INVENTION

The present invention provides a novel neuronal growth factor, Narp, (neuronal-activity regulated pentraxin), which is highly potent in inducing enhanced growth of neuronal dendritic processes.

In a first embodiment, the invention provides Narp polypeptide and isolated polynucleotides encoding Narp.

In another embodiment, the invention provides a method for inducing growth of a neuronal cell by contacting the cell with an amount of Narp polypeptide or a Narp encoding polynucleotide (in operable linkage with appropriate transcription elements) effective for inducing growth of the neuron. Neuronal cell can be induced either in vitro or in vivo.

In another embodiment, the invention provides a method for inducing migration of a neuronal cell by contacting the cell with an amount of Narp polypeptide or a Narp encoding polynucleotide effective for inducing migration of the neuron.

In one aspect of the invention, diagnostic methods are provided including contact a sample suspected of containing Narp with either a nucleic acid or immunodiagnostic reagent.

In yet another embodiment, the invention provides a method for treating a subject having a neuronal cell disorder by administering to the subject a therapeutically effective amount of Narp polypeptide or Narp encoding polynucleotide. Such disorders may include stroke, cerebral palsy and various degenerative diseases, for example.

BRIEF DESCRIPTION OF THE DRAWINGS

FIGS. 1A–B shows the nucleotide sequence of Narp cDNA and its predicted amino acid sequence (SEQ ID NO: 1 Narp cDNA nucleotide sequence, and SEQ ID NO: 2 Narp amino acid). The last nucleotide of each line is numbered to the right. The translated protein sequence is shown below corresponding nucleotide sequence and is numbered on the left side. The putative signal peptide of 16 amino acids is underlined. A dot indicates the predicted first amino acid of the mature protein. Putative glycosylation sites are circled. Two putative ATTTA mRNA instability motifs are present in the 3'-untranslated region and are boxed. The putative polyadenylation signal (ATTAAA) is underlined.

FIGS. 2A–B shows a comparison of rat Narp amino acid sequence (SEQ ID:5) with rat CRP (SEQ ID:4), rat SAP (SEQ ID:3), guinea pig apexin (deduced from cDNA) and human NPII (predicted sequence from human genomic clone; Hsu and Perin, *Genomics* 28:220, 1995). A) The full-length amino acid sequences of rat CRP and SAP are shown with the corresponding homologous region of Narp. Identical amino acid residues are boxed. The eight amino acid "pentraxin family signature" is marked in bold-face. The β-strand regions defined by X-ray crystallography of human SAP (Emsley et al., supra) are indicated by letter A–O and a single overline above the corresponding residues. Residues involved in calcium binding are indicated by a dot; Asp 58, Asn 59, Glu 136, Gln 137, Asp 138, and Gln 148. Conserved cysteine residues 36 and 95 are highlighted by an asterisk. B) Full length Narp (SEQ ID:2) is compared to guinea pig Apexin (SEQ ID:6) and human NPII (SEQ ID:7). Regions that are identical in all three sequences are boxed while regions identical between two are shaded.

DESCRIPTION OF THE PREFERRED EMBODIMENTS

Figure 3A:
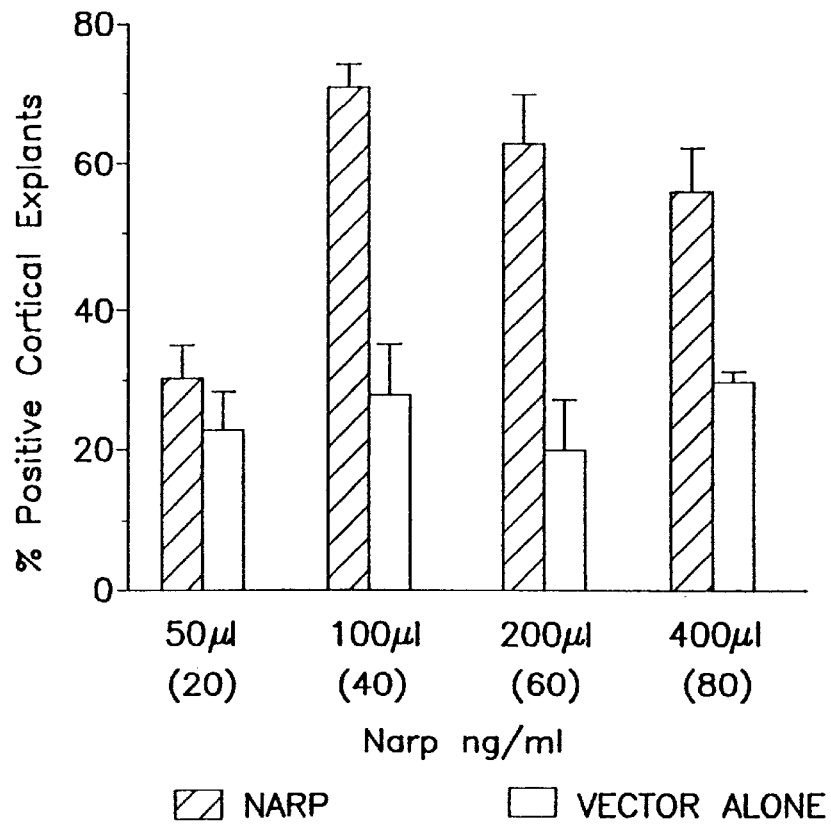
FIGS. 3A–B is a bar graph showing the results of a neurite outgrowth assay with partially purified myc-tagged Narp. A) Partially purified myc Narp induces neurite outgrowth. Cortical explants from postnatal day 1 rat pups were cultured on poly-L-ornithine coated plates. myc-tagged Narp was partially purified by agar affinity chromatography from COS-1 cell supernatant and aliquots were added to culture media. The amount of myc-tagged Narp was determined by ELISA. After 24 hrs, the number of explants with neurite outgrowth was determined and expressed as the percent of the total number of cortical explants. Data are from three separate experiments each performed in duplicate. Neurite outgrowth is observed with ~40 ng/ml of Narp. Control experiments used identical volumes of agar column fractions prepared from conditioned media of COS-1 cells transfected with vector alone. Explants treated with the control fractions demonstrate a 20–30% spontaneous outgrowth. B) Immunodepletion with myc antibody blocks neurite outgrowth activity. Partially purified myc-tagged Narp (~50 ng in 200 $\mu$l) was immunodepleted using mouse anti-myc antibody conjugated to protein G-agarose beads. Control experiments substituted mouse ascites for anti-myc antibody. Immunodepleted and control fractions were added to media and neurite outgrowth was assayed after 24 hrs. Data are from two separate experiments each performed in quadruplicate.
Figure 3B:
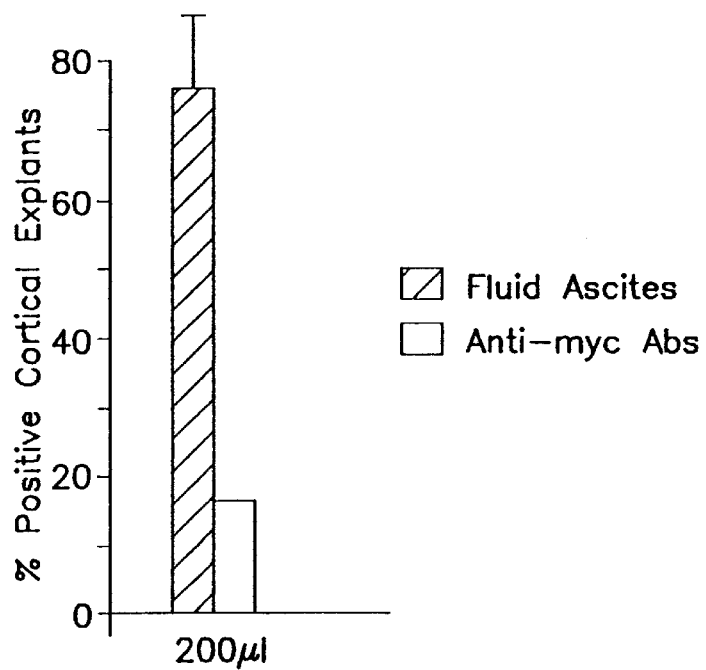

The present invention provides a novel neuronal growth factor, Narp (neuronal activity-regulated pentraxin. Narp promotes neuronal cell migration and neurite (e.g., neuronal dendrite) outgrowth, at dosages comparable to known neurotrophins and growth factors. Narp is regulated by physiological synaptic activity and may be involved in neural development and activity-dependent neuronal plasticity. Hence, Narp may have in vitro and in vivo applications in the treatment of neurodegenerative diseases, such as amyotrophic lateral sclerosis, or in maintaining cells or tissues in culture prior to transplantation.

Many growth factors have expression patterns or possess activities that relate to the function of the nervous system. For example, one growth factor in the TGF family, namely GDNF, has been shown to be a potent neurotrophic factor that can promote the survival of dopaminergic neurons (Lin, et al., *Science*, 260:1130). Another family member, namely dorsalin-1, is capable of promoting the differentiation of neural crest cells (Basler, et al., *Cell*, 73:687, 1993). The inhibins and activins have been shown to be expressed in the brain (Meunier, et al., *Proc. Nat'l. Acad. Sci., USA*, 85:247, 1988; Sawchenko, et al., *Nature*, 334:615, 1988; Andreasson and Worley, *Neurosci.* 69:781, 1995), and activin has been shown to be capable of functioning as a nerve cell survival molecule (Schubert, et al., Nature, 344:868, 1990). Another TGF family member, namely GDF-1, is nervous system-specific in its expression pattern (Lee, *Proc. Nat'l. Acad. Sci., USA*, 88:4250, 1991), and certain other family members, such as Vgr-1 (Lyons, et al., *Proc. Nat'l. Acad. Sci., USA*, 86:4554, 1989; Jones, et al., *Development*, 111:581, 1991), OP-1 (Ozkaynak, et al., *J. Biol. Chem.*, 267:25220, 1992), and BMP-4 (Jones, et al., *Development*, 111:531, 1991), are also known to be expressed in the nervous system.

The expression of Narp in the brain suggests that Narp may also possess activities that relate to the function of the nervous system. Narp may have neurotrophic activities for various neuronal populations. Hence, Narp may have in vitro and in vivo applications in the treatment of neurodegenerative diseases, such as amyotrophic lateral sclerosis, in disorders whose etiology is at least in part from a failure of neurons to survive and grow normally, such as stroke or epilepsy, or in maintaining cells or tissues in culture prior to transplantation.

Narp may also play a role in establishment of long-term neuroplasticity. Long term potentiation, or LTP, is a persistent, activity-dependent form of synaptic modification that can be induced by brief, high-frequency stimulation of neurons (i.e., the strengthening of the synaptic connection between two neurons). The maintenance of LTP may involve both presynaptic and postsynaptic mechanisms (for review, see Bliss & Collingridge, *Nature*, 361:31–39, 1993). This increase is understood to signify that LTP is associated with enhanced cognitive function. LTP was first discovered in 1966 to result from a response to high frequency electrical stimulation (tetanus) of the axons in the perforant path with a burst of approximately one hundred pulses of electrical stimulation, delivered within a few seconds. Evidence that LTP has occurred is obtained by periodically delivering single pulses to the perforant path and recording the response in the dentate gyrus. If, for example, the population excitatory post synaptic potential (EPSP) is larger than it was before tetanus, LTP has taken place. LTP can also be produced in fields CA3 and CA1 as well as in the neocortex (Perkins and Teyler, *Brain Research*, 439:25–47, 1988; Brown, et al., in *Neural Models of Plasticity: Experimental and Theoretical Approaches*, ed. J. H. Byrne and W. O. Berry, San Diego: Academic Press, 1989). It can last for several months (Bliss and Lømo, *J. Physiol.*, 232:331, 1973). Even more importantly, LTP can involve the interaction between different synapses on a particular neuron. That is, when weak and strong synapses on a single neuron are stimulated at approximately the same time, the weak synapse becomes strengthened, and this strengthening of the synapse has been proposed to be the basis of long-term learning (Hebb, *The Organization of Behavior*, New York: Wiley-Interscience, 1949). This phenomenon, produced by the association (in time) between the activity of two synapses, is called associative LTP because it resembles what happens during classical conditioning for learned responses.

There is evidence to suggest that synthesis of new proteins is necessary for LTP. Expression of the immediate early genes zif/268 and c-fos is induced by tetanic stimulation, and is blocked by NMDA receptor antagonists. These results indicate that calcium signalling is required for the induction of immediate early genes. Furthermore, after tetanization, protein kinase C mRNA is down regulated, whereas mRNA encoding $Ca^{2+}$/calmodium-dependent protein kinase is up-regulated. Thus, altered gene expression may play a role in induction, expression and/or maintenance of LTP.

Narp mRNA is dynamically regulated by physiological synaptic activity in the adult hippocampus and visual cortex. In the hippocampus, synaptic induction of Narp is associated with the production of LTP and is dependent on a glutamate receptor, the NMDA receptor. Other glutamate receptors, such as AMPA, may also be associated with expression of Narp or other pentraxin family members. Identical numbers of synaptic stimuli administered at low frequency which do not activate the NMDA receptor, do not induce Narp. Also like other IEGs, Narp is expressed at relatively high levels by neurons in the adolescent and adult neocortex, where natural synaptic activity is dependent, to a substantial degree on NMDA receptor activation. Thus, Narp expression is specifically associated with the specific forms of synaptic activity that activate the NMDA receptor and induce long-term neuronal plasticity.

Figure 1A:
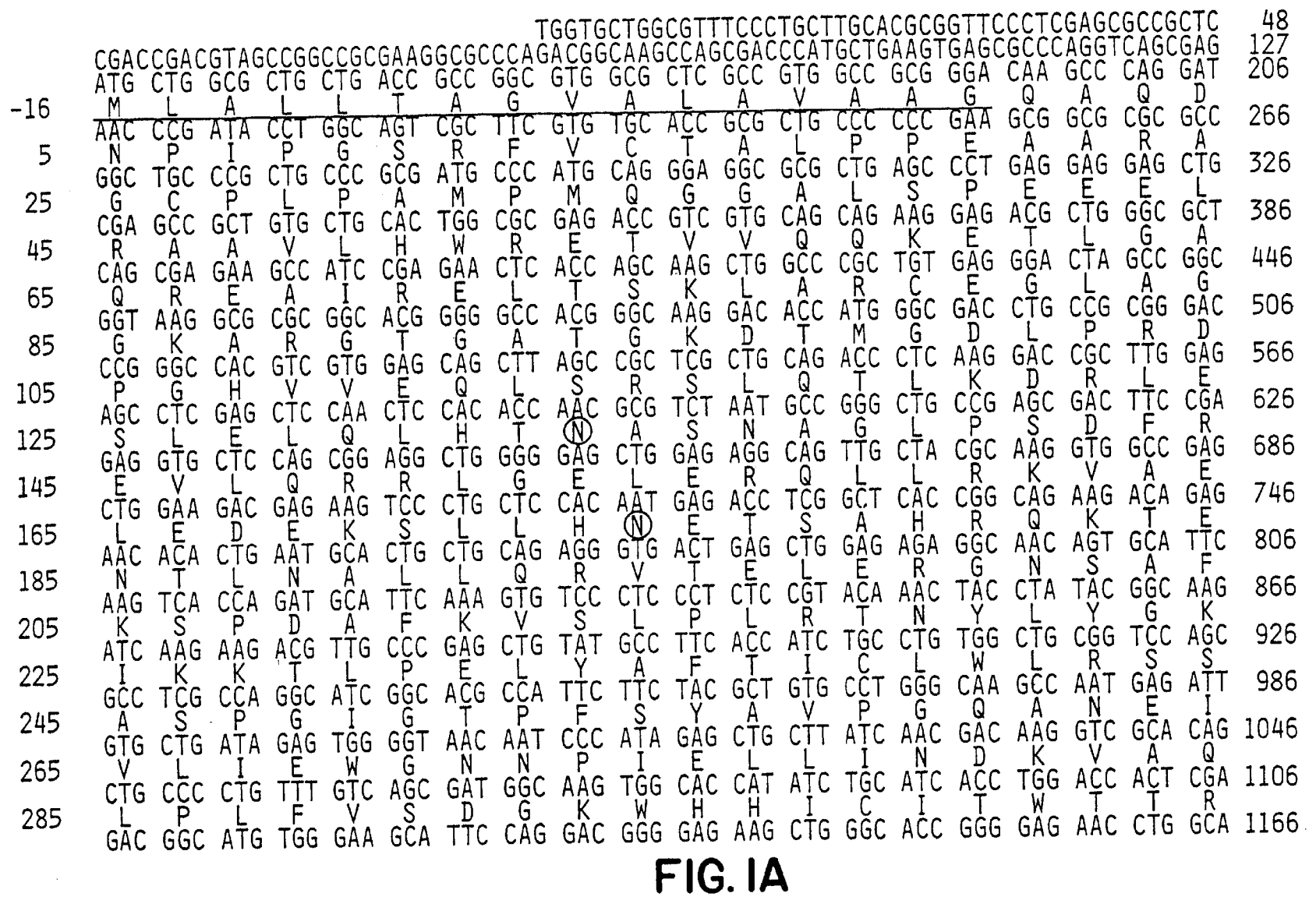

In a first embodiment, the present invention provides a substantially pure Narp polypeptide. Narp polypeptide is exemplified by the amino acid sequence shown in FIG. 1 and SEQ ID NO:2. Narp polypeptide is characterized as having a predicted molecular weight of 46.2 kDa and a pI of 5.46. There is an amino terminal secretory signal peptide sequence predicted using methods from von Heijne (von Heijne, G., Nucl Acids Res., 14:4683, 1986). The predicted cleavage site is between glycine and glutamine. Three potential N-linked glycosylation sites are found at amino acid residues 133, 174 and 378 (nomenclature refers to numbering beginning at the N-terminus in FIG. 1 herein).

Figure 2A:
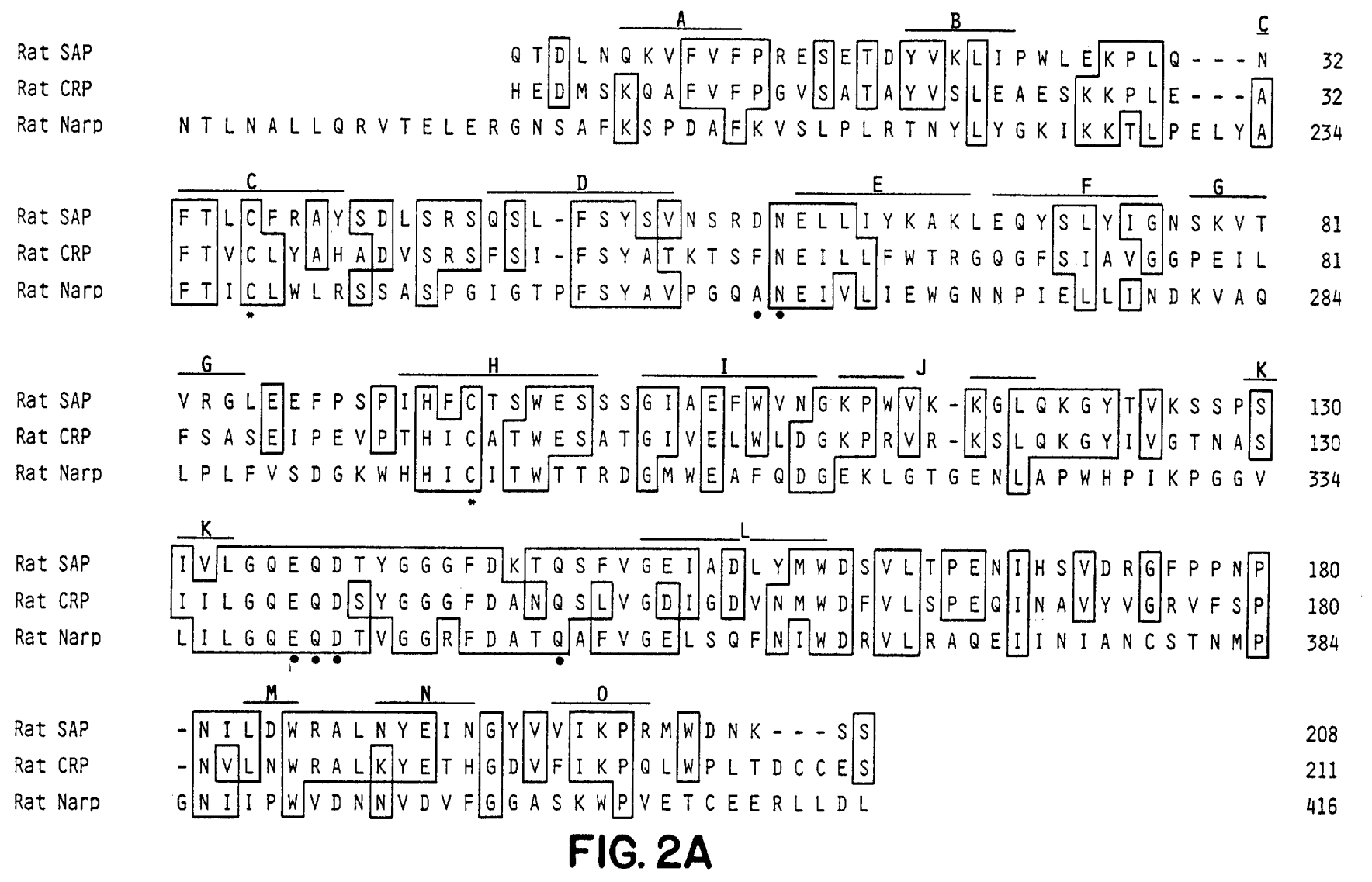

Narp polypeptide is 24% and 26% identical to C-reactive protein (CRP) and serum amyloid B component (SAP), respectively, over a 210 amino acid span that includes the full length sequence of mature CRP and SAP and the carboxyl terminal 216 amino acids of Narp. FIG. 2A shows the alignment of Narp with rat CRP and SAP. Islands of homology are clustered throughout the sequence. Eight amino acids have been identified that constitute the "pentraxin family signature" sequence (H-X-C-X-S/T-W-X-S/T) (SEQ ID:8) which is present in all pentraxin family members and is also present in Narp. Narp also contains calcium binding domains and calcium-dependent lectin properties of the pentraxin family.

The term "substantially pure" as used herein refers to Narp polypeptide which is substantially free of other proteins, lipids, carbohydrates or other materials with which it is naturally associated. One skilled in the art can purify Narp using standard techniques for protein purification. Alternatively, two preferred methods for Narp polypeptide purification include agar affinity chromatography and wheat germ agglutinin binding (see Examples herein). The substantially pure polypeptide will yield a single major band of about 44 kD (non-glycosylated) or 58 kD (glycosylated) on a reducing polyacrylamide gel. The purity of the Narp polypeptide can also be determined by amino-terminal amino acid sequence analysis.

The invention includes a functional polypeptide, Narp, and functional fragments thereof. As used herein, the term "functional polypeptide" refers to a polypeptide which possesses a biological function or activity which is identified through a defined functional assay and which is associated with a particular biologic, morphologic, or phenotypic alteration in the cell. Functional fragments of the Narp polypeptide, includes fragments of Narp as long as the activity, e.g., induction of neurite outgrowth, of Narp remains. Smaller peptides containing the biological activity of Narp are included in the invention.

The neurite or neuronal dendritic growth promoting effects of Narp or the migration effect on neurons are useful for bioassays to identify biologically active fragments of Narp polypeptide. Further, these novel bioassays are useful for identifying other pentraxins, for example, having neurite outgrowth promoting activity or neuronal migration promoting activity. For example, as described in the examples herein (see in particular, Example 1, 12.), cortical explants can be co-cultured with cells expressing Narp polynucleotide or fragments thereof. Further, if desirable, a similar assay can be performed to identify small molecules (including Narp peptides or chemical molecules, for example) that block Narp's growth promoting effects. Narp may act as "kindling" in disorders such as epilepsy, by contributing to sustained and increased excitability of dendrites through its neurite outgrowth promoting activity. Consequently, it would be desirable to block Narp's growth promoting effects in such disorders. Further, blocking Narp's migration promoting activity might be useful for treatment of various neuronal tumors, and also including glial cell tumors.

As used herein, the term "neurite" outgrowth includes dendritic and axonal outgrowth from neuronal cells. One of skill in the art will be familiar with the term neurite. More often, Narp activity is associated with dendritic outgrowth, and therefore the term "dendritic" growth or outgrowth is often used herein.

The biological function, for example, can vary from a polypeptide fragment as small as an epitope to which an antibody molecule can bind to a large polypeptide which is capable of participating in the characteristic induction or programming of phenotypic changes within a cell. A "functional polynucleotide" denotes a polynucleotide which encodes a functional polypeptide as described herein.

Figure 1B:
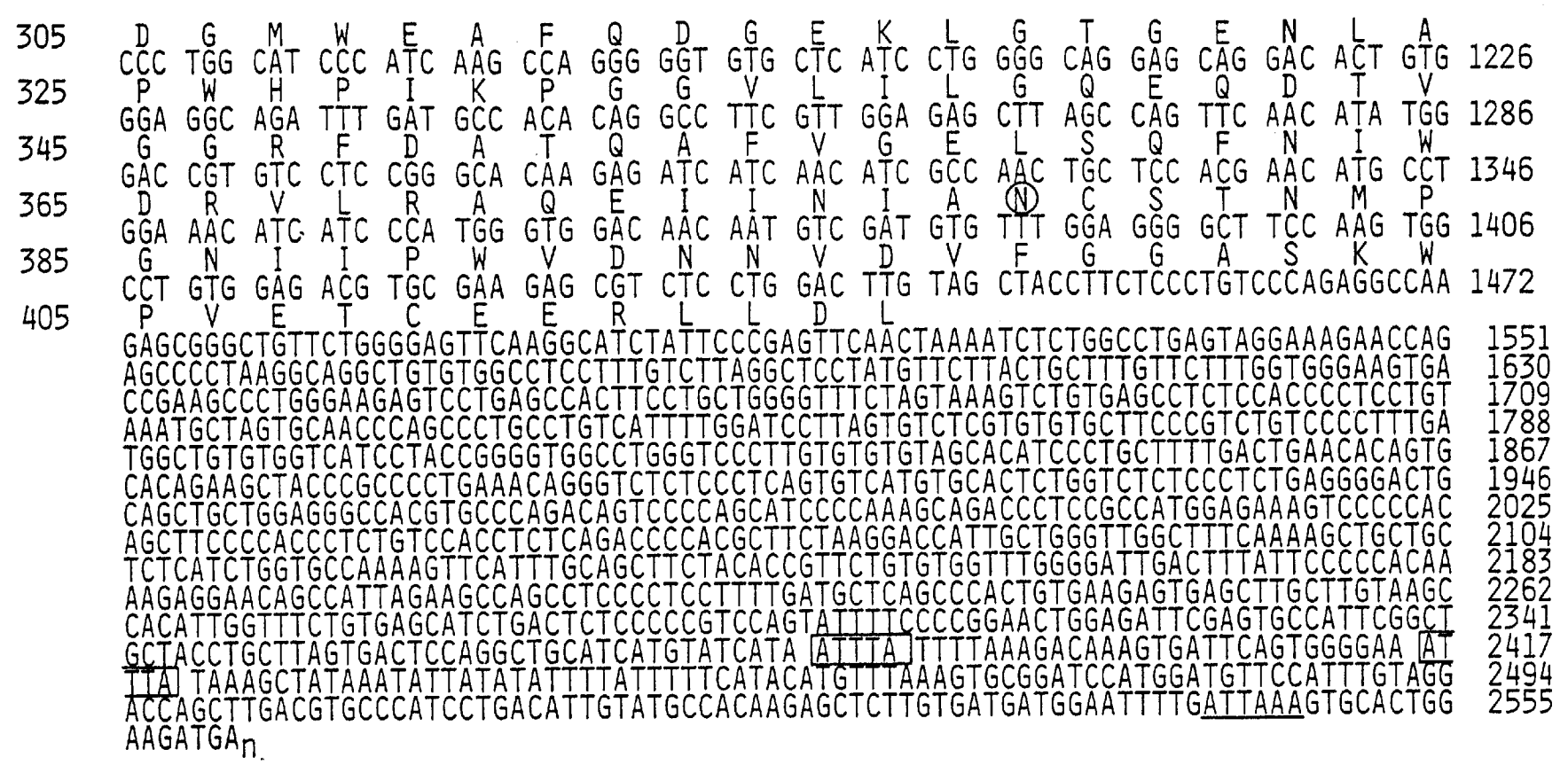

Minor modifications of the Narp primary amino acid sequence may result in proteins which have substantially equivalent activity as compared to the Narp polypeptide described herein in SEQ ID NO:2 (FIG. 1). Such modifications may be deliberate, as by site-directed mutagenesis, or may be spontaneous. All of the polypeptides produced by these modifications are included herein as long as the biological activity of Narp is present, e.g., promotion of neurite outgrowth. Further, deletion of one or more amino acids can also result in a modification of the structure of the resultant molecule without significantly altering its activity. This can lead to the development of a smaller active molecule which would have broader utility. For example, it is possible to remove amino or carboxy terminal amino acids which may not be required for Narp activity.

The Narp polypeptide of the invention also includes conservative variations of the polypeptide sequence. The term "onservative variation" as used herein denotes the replacement of an amino acid residue by another, biologically similar residue. Examples of conservative variations include the substitution of one hydrophobic residue such as isoleucine, valine, leucine or methionine for another, or the substitution of one polar residue for another, such as the substitution of arginine for lysine, glutamic for aspartic acids, or glutamine for asparagine, and the like. The term "conservative variation" also includes the use of a substituted amino acid in place of an unsubstituted parent amino acid provided that antibodies raised to the substituted polypeptide also immunoreact with the unsubstituted polypeptide.

The invention also provides an isolated polynucleotide sequence encoding a polypeptide having the amino acid sequence of SEQ ID NO:2. The term "isolated" as used herein includes polynucleotides substantially free of other nucleic acids, proteins, lipids, carbohydrates or other materials with which it is naturally associated. Polynucleotide sequences of the invention include DNA, cDNA and RNA sequences which encode Narp. It is understood that all polynucleotides encoding all or a portion of Narp are also included herein, as long as they encode a polypeptide with Narp activity. Such polynucleotides include naturally occurring, synthetic, and intentionally manipulated polynucleotides. For example, portions of the mRNA sequence may be altered due to alternate RNA splicing patterns or the use of alternate promoters for RNA transcription. As another example, Narp polynucleotide may be subjected to site-directed mutagenesis. The polynucleotide sequence for Narp also includes antisense sequences. The polynucleotides of the invention include sequences that are degenerate as a result of the genetic code. There are 20 natural amino acids, most of which are specified by more than one codon. Therefore, all degenerate nucleotide sequences are included in the invention as long as the amino acid sequence of Narp polypeptide encoded by the nucleotide sequence is functionally unchanged. In addition, the invention also includes a polynucleotide encoding a polypeptide having the biological activity of an amino acid sequence of SEQ ID NO:2 and having at least one epitope for an antibody immunoreactive with Narp polypeptide.

The polynucleotide encoding Narp includes the nucleotide sequence in FIG. 1 (SEQ ID NO:1), as well as nucleic acid sequences complementary to that sequence. A complementary sequence may include an antisense nucleotide. When the sequence is RNA, the deoxyribonucleotides A, G, C, and T of FIG. 1 are replaced by ribonucleotides A, G, C, and U, respectively. Also included in the invention are fragments (portions) of the above-described nucleic acid sequences that are at least 15 bases in length, which is sufficient to permit the fragment to selectively hybridize to DNA that encodes the protein of FIG. 1 (SEQ ID NO: 2). "Selective hybridization" as used herein refers to hybridization under moderately stringent or highly stringent physiological conditions (See, for example, the techniques described in Maniatis et al., 1989 Molecular Cloning A Laboratory Manual, Cold Spring Harbor Laboratory, N.Y., incorporated herein by reference), which distinguishes related from unrelated nucleotide sequences.

Specifically disclosed herein is a cDNA sequence for Narp. A novel cDNA corresponding to the 3' non-coding region of a ~2.5 kilobase (kb) mRNA was identified by differential screening of a subtracted cDNA library prepared from seizure stimulated hippocampus. The size of the cDNA (2561 bp) corresponds closely to the estimated size of the mRNA determined by Northern analysis. The longest open reading frame (ORF) with an initiator methionine predicts a 432 amino acid protein. A second, independent clone (2460 bp which begins at nucleotide 101 (from 5' end) of the longest clone) contains the entire ORF, and the nucleotide and the predicted amino acid sequences are identical to those of the longer clone. While not wanting to be bound by a particular theory, it appears that the Narp mRNA in the brain is rapidly induced (IEG), with transient expression of Narp, while Narp mRNA in the testes exhibits constitutive expression. The brain mRNA species is typically longer than the testes species and contains a longer 3' non-translated sequence. The full length brain mRNA is depicted in FIG. 1.

FIG. 1 shows the complete Narp cDNA and deduced protein sequences (SEQ ID NO:1 and 2, respectively). The initiator methionine was selected to be the best Kozak consensus for translation initiation and occurs at nucleotide 128 of the longest cDNA. The ORF continues to the 5' end of the cDNA and there is no frame stop 5' to the predicted initiator methionine. Alternative initiator methionine are present at nucleotides 265, 271 and 466 (from 5' end). The identified location of the translation start site is supported by analysis of the in vitro transcription/translation products. The 3' non-coding region contains the ATTA motif in positions 2362 and 2396 which may contribute to the rapid turnover of Narp mRNA and is present in many IEGs. No classical polyadenylation signal sequence (AATAAA) was identified; however, the sequence ATTAAA is present in 5 independent clones 21 nucleotides from the 3' terminal poly(A) tail.

DNA sequences of the invention can be obtained by several methods. For example, the DNA can be isolated using hybridization or computer-based techniques which are well known in the art. These include, but are not limited to: 1) hybridization of genomic or cDNA libraries with probes to detect homologous nucleotide sequences; 2) antibody screening of expression libraries to detect cloned DNA fragments with shared structural features; 3) polymerase chain reaction (PCR) on genomic DNA or cDNA using primers capable of annealing to the DNA sequence of interest; 4) computer searches of sequence databases for similar sequences; and 5) differential screening of a subtracted DNA library.

Preferably the Narp polynucleotide of the invention is derived from a mammalian organism. Screening procedures which rely on nucleic acid hybridization make it possible to isolate any gene sequence from any organism, provided the appropriate probe is available. Oligonucleotide probes, which correspond to a part of the sequence encoding the protein in question, can be synthesized chemically. This requires that short, oligopeptide stretches of amino acid sequence must be known. The DNA sequence encoding the protein can be deduced from the genetic code, however, the degeneracy of the code must be taken into account. It is possible to perform a mixed addition reaction when the sequence is degenerate. This includes a heterogeneous mixture of denatured double-stranded DNA. For such screening, hybridization is preferably performed on either single-stranded DNA or denatured double-stranded DNA. Hybridization is particularly useful in the detection of cDNA clones derived from sources where an extremely low amount of mRNA sequences relating to the polypeptide of interest are present. In other words, by using stringent hybridization conditions directed to avoid non-specific binding, it is possible, for example, to allow the autoradiographic visualization of a specific cDNA clone by the hybridization of the target DNA to that single probe in the mixture which is its complete complement (Wallace, et al., *Nucl. Acid Res.*, 9:879, 1981). Alternatively, a subtractive library, as illustrated herein is useful for elimination of non-specific cDNA clones.

When the entire sequence of amino acid residues of the desired polypeptide is not known, the direct synthesis of DNA sequences is not possible and the method of choice is the synthesis of cDNA sequences. Among the standard procedures for isolating cDNA sequences of interest is the formation of plasmid- or phage-carrying cDNA libraries which are derived from reverse transcription of MRNA which is abundant in donor cells that have a high level of genetic expression. When used in combination with polymerase chain reaction technology, even rare expression products can be cloned. In those cases where significant portions of the amino acid sequence of the polypeptide are known, the production of labeled single or double-stranded DNA or RNA probe sequences duplicating a sequence putatively present in the target cDNA may be employed in DNA/DNA hybridization procedures which are carried out on cloned copies of the cDNA which have been denatured into a single-stranded form (Jay, et al., *Nucl. Acid Res.*, 11:2325, 1983).

A cDNA expression library, such as lambda gt11, can be screened indirectly for Narp peptides having at least one epitope, using antibodies specific for Narp. Such antibodies can be either polyclonally or monoclonally derived and used to detect expression product indicative of the presence of Narp cDNA.

Alterations in Narp nucleic acid include intragenic mutations (e.g., point mutation, nonsense (stop), missense, splice site and frameshift) and heterozygous or homozygous deletions. Detection of such alterations can be done by standard methods known to those of skill in the art including sequence analysis, Southern blot analysis, PCR based analyses (e.g., multiplex PCR, sequence tagged sites (STSs)) and in situ hybridization. Such proteins can be analyzed by standard SDS-PAGE and/or immunoprecipitation analysis and/or Western blot analysis, for example. In addition, the in vitro synthesized (IVS) protein assay as described in the present examples can be used to analyze Narp protein product.

DNA sequences encoding Narp can be expressed in vitro by DNA transfer into a suitable host cell. "Host cells" are cells in which a vector can be propagated and its DNA expressed. The term also includes any progeny of the subject host cell. It is understood that all progeny may not be identical to the parental cell since there may be mutations that occur during replication. However, such progeny are included when the term "host cell" is used. Methods of stable transfer, meaning that the foreign DNA is continuously maintained in the host, are known in the art.

In the present invention, the Narp polynucleotide sequences may be inserted into a recombinant expression vector. The term "recombinant expression vector" refers to a plasmid, virus or other vehicle known in the art that has been manipulated by insertion or incorporation of the Narp genetic sequences. Such expression vectors contain a promoter sequence which facilitates the efficient transcription of the inserted genetic sequence of the host. The expression vector typically contains an origin of replication, a promoter, as well as specific genes which allow phenotypic selection of the transformed cells. Vectors suitable for use in the present invention include, but are not limited to the T7-based expression vector for expression in bacteria (Rosenberg, et al., *Gene*, 56:125, 1987), the pMSXND expression vector for expression in mammalian cells (Lee and Nathans, *J. Biol. Chem.*, 263:3521, 1988) and baculovirus-derived vectors for expression in insect cells. The DNA segment can be present in the vector operably linked to regulatory elements, for example, a promoter (e.g., T7, metallothionein I, or polyhedrin promoters).

Polynucleotide sequences encoding Narp can be expressed in either prokaryotes or eukaryotes. Hosts can include microbial, yeast, insect and mammalian organisms. However, since mature Narp is glycosylated, the choice of host cells depends on whether or not the glycosylated or non-glycosylated form of Narp. Methods of expressing DNA sequences having eukaryotic or viral sequences in prokaryotes are well known in the art. Biologically functional viral and plasmid DNA vectors capable of expression and replication in a host are known in the art. Such vectors are used to incorporate DNA sequences of the invention.

Methods which are well known to those skilled in the art can be used to construct expression vectors containing the Narp coding sequence and appropriate transcriptional/translational control signals. These methods include in vitro recombinant DNA techniques, synthetic techniques, and in vivo recombination/genetic techniques. (See, for example, the techniques described in Maniatis et al., 1989 Molecular Cloning A Laboratory Manual, Cold Spring Harbor Laboratory, N.Y.).

A variety of host-expression vector systems may be utilized to express the Narp coding sequence. These include but are not limited to microorganisms such as bacteria transformed with recombinant bacteriophage DNA, plasmid DNA or cosmid DNA expression vectors containing the Narp coding sequence; yeast transformed with recombinant yeast expression vectors containing the Narp coding sequence; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing the Narp coding sequence; insect cell systems infected with recombinant virus expression vectors (e.g., baculovirus) containing the Narp coding sequence; or animal cell systems infected with recombinant virus expression vectors (e.g., retroviruses, adenovirus, vaccinia virus) containing the Narp coding sequence, or transformed animal cell systems engineered for stable expression. Since Narp has not been confirmed to contain carbohydrates, both bacterial expression systems as well as those that provide for translational and post-translational modifications may be used; e.g., mammalian, insect, yeast or plant expression systems.

Depending on the host/vector system utilized, any of a number of suitable transcription and translation elements, including constitutive and inducible promoters, transcription enhancer elements, transcription terminators, etc. may be used in the expression vector (see e.g., Bitter et al., 1987, Methods in Enzymology 153:516–544). For example, when cloning in bacterial systems, inducible promoters such as pL of bacteriophage γ, plac, ptrp, ptac (ptrp-lac hybrid promoter) and the like may be used. When cloning in mammalian cell systems, promoters derived from the genome of mammalian cells (e.g., metallothionein promoter) or from mammalian viruses (e.g., the retrovirus long terminal repeat; the adenovirus late promoter; the vaccinia virus 7.5K promoter) may be used. Promoters produced by recombinant DNA or synthetic techniques may also be used to provide for transcription of the inserted Narp coding sequence.

In bacterial systems a number of expression vectors may be advantageously selected depending upon the use intended for the expressed protein. For example, when large quantities of non-glycosylated Narp are to be produced, vectors which direct the expression of high levels of fusion protein products that are readily purified may be desirable. Those which are engineered to contain a cleavage site to aid in recovering are preferred. Such vectors include but are not limited to the *E. coli* expression vector pUR278 (Ruther et al., *EMBO J.* 2:1791, 1983), in which the Narp coding sequence may be ligated into the vector in frame with the lac Z coding region so that a hybrid -lac Z protein is produced; pIN vectors (Inouye & Inouye, 1985, Nucleic acids Res. 13:3101–3109; Van Heeke & Schuster, 1989, *J. Biol. Chem.* 264:5503–5509); and the like. In yeast, a number of vectors containing constitutive or inducible promoters may be used. For a review see, Current Protocols in Molecular Biology, Vol. 2, 1988, Ed. Ausubel et al., Greene Publish. Assoc. & Wiley Interscience, Ch. 13; Grant et al., 1987, Expression and Secretion Vectors for Yeast, in Methods in Enzymology, Eds. Wu & Grossman, 31987, Acad. Press, N.Y., Vol. 153, pp.516–544; Glover, 1986, DNA Cloning, Vol. II, IRL Press, Wash., D.C., Ch. 3; and Bitter, 1987, Heterologous Gene Expression in Yeast, Methods in Enzymology, Eds. Berger & Kimmel, Acad. Press, N.Y., Vol. 152, pp. 673–684; and The Molecular Biology of the Yeast Saccharomyces, 1982, Eds. Strathern et al., Cold Spring Harbor Press, Vols. I and II. A constitutive yeast promoter such as ADH or LEU2 or an inducible promoter such as GAL may be used (Cloning in Yeast, Ch. 3, R. Rothstein In: DNA Cloning Vol.11, A Practical Approach, Ed. D M Glover, 1986, IRL Press, Wash., D.C.). Alternatively, vectors may be used which promote integration of foreign DNA sequences into the yeast chromosome.

Eukaryotic systems, and preferably mammalian expression systems, allow for proper post-translational modifications of expressed mammalian proteins to occur. Eukaryotic cells which possess the cellular machinery for proper processing of the primary transcript, glycosylation, phosphorylation, and advantageously, secretion of the gene product may be used as host cells for the expression of Narp. Mammalian cell lines may be preferable. Such host cell lines may include but are not limited to CHO, VERO, BHK, HeLa, COS, MDCK, −293, and WI38.

Mammalian cell systems which utilize recombinant viruses or viral elements to direct expression may be engineered. For example, when using adenovirus expression vectors, the Narp coding sequence may be ligated to an adenovirus transcription/translation control complex, e.g., the late promoter and tripartite leader sequence. Alternatively, the vaccinia virus 7.5K promoter may be used. (e.g., see, Mackett et al., 1982, Proc. Natl. Acad. Sci. USA 79: 7415–7419; Mackett et al., 1984, J. Virol. 49: 857–864; Panicali et al., 1982, Proc. Natl. Acad. Sci. USA 79: 4927–4931). Of particular interest are vectors based on bovine papilloma virus which have the ability to replicate as extrachromosomal elements (Sarver, et al., 1981, Mol. Cell. Biol. 1: 486). Shortly after entry of this DNA into mouse cells, the plasmid replicates to about 100 to 200 copies per cell. Transcription of the inserted cDNA does not require integration of the plasmid into the host's chromosome, thereby yielding a high level of expression. These vectors can be used for stable expression by including a selectable marker in the plasmid, such as, for example, the neo gene. Alternatively, the retroviral genome can be modified for use as a vector capable of introducing and directing the expression of the Narp gene in host cells (Cone & Mulligan, 1984, Proc. Natl. Acad. Sci. USA 81:6349–6353). High level expression may also be achieved using inducible promoters, including, but not limited to, the metallothionine IIA promoter and heat shock promoters.

For long-term, high-yield production of recombinant proteins, stable expression is preferred. Rather than using expression vectors which contain viral origins of replication, host cells can be transformed with the Narp cDNA controlled by appropriate expression control elements (e.g., promoter, enhancer, sequences, transcription terminators, polyadenylation sites, etc.), and a selectable marker. The selectable marker in the recombinant plasmid confers resistance to the selection and allows cells to stably integrate the plasmid into their chromosomes and grow to form foci which in turn can be cloned and expanded into cell lines. For example, following the introduction of foreign DNA, engineered cells may be allowed to grow for 1–2 days in an enriched media, and then are switched to a selective media. A number of selection systems may be used, including but not limited to the herpes simplex virus thymidine kinase (Wigler,et al., 1977, Cell 11: 223), hypoxanthine-guanine phosphoribosyltransferase (Szybalska & Szybalski, 1962, Proc. Natl. Acad. Sci. USA 48: 2026), and adenine phosphoribosyltransferase (Lowy, et al., 1980, Cell 22: 817) genes can be employed in tk-, hgprt- or aprt- cells respectively. Also, antimetabolite resistance can be used as the basis of selection for dhfr, which confers resistance to methotrexate (Wigler, et al., 1980, Natl. Acad. Sci. USA 77: 3567; O'Hare, et al., 1981, Proc. Natl. Acad. Sci. USA 78: 1527); gpt, which confers resistance to mycophenolic acid (Mulligan & Berg, 1981, Proc. Natl. Acad. Sci. USA 78: 2072; neo, which confers resistance to the aminoglycoside G-418 (Colberre-Garapin, et al., 1981, J. Mol. Biol. 150: 1); and hygro, which confers resistance to hygromycin (Santerre, et al., 1984, Gene 30: 147) genes. Recently, additional selectable genes have been described, namely trpB, which allows cells to utilize indole in place of tryptophan; hisD, which allows cells to utilize histinol in place of histidine (Hartman & Mulligan, 1988, Proc. Natl. Acad. Sci. USA 85: 8047); and ODC (ornithine decarboxylase) which confers resistance to the ornithine decarboxylase inhibitor, 2-(difluoromethyl)-DL-ornithine, DFMO (McConlogue L., 1987, In: Current Communications in Molecular Biology, Cold Spring Harbor Laboratory ed.).

Transformation of a host cell with recombinant DNA may be carried out by conventional techniques as are well known to those skilled in the art. Where the host is prokaryotic, such as E. coli, competent cells which are capable of DNA uptake can be prepared from cells harvested after exponential growth phase and subsequently treated by the $CaCl_2$ method using procedures well known in the art. Alternatively, $MgCl_2$ or RbCl can be used. Transformation can also be performed after forming a protoplast of the host cell if desired.

When the host is a eukaryote, such methods of transfection of DNA as calcium phosphate co-precipitates, conventional mechanical procedures such as microinjection, electroporation, insertion of a plasmid encased in liposomes, or virus vectors may be used. Eukaryotic cells can also be cotransformed with DNA sequences encoding the Narp of the invention, and a second foreign DNA molecule encoding a selectable phenotype, such as the herpes simplex thymidine kinase gene. Another method is to use a eukaryotic viral vector, such as simian virus 40 (Sv40) or bovine papilloma virus, to transiently infect or transform eukaryotic cells and express the protein. (see for example, *Eukaryotic Viral Vectors*, Cold Spring Harbor Laboratory, Gluzman ed., 1982).

Isolation and purification of microbial expressed polypeptide, or fragments thereof, provided by the invention, may be carried out by conventional means including preparative chromatography and immunological separations involving monoclonal or polyclonal antibodies.

The invention includes antibodies immunoreactive with Narp polypeptide or antigenic fragments thereof. Antibody which consists essentially of pooled monoclonal antibodies with different epitopic specificities, as well as distinct monoclonal antibody preparations are provided. Monoclonal antibodies are made from antigen containing fragments of the protein by methods well known to those skilled in the art (Kohler, et al., Nature, 256:495, 1975).

The term "antibody" as used in this invention includes intact molecules as well as fragments thereof, such as Fab, F(ab')2, and Fv which are capable of binding the epitopic determinant. These antibody fragments retain some ability to selectively bind with its antigen or receptor and are defined as follows:

(1) Fab, the fragment which contains a monovalent antigen-binding fragment of an antibody molecule can be produced by digestion of whole antibody with the enzyme papain to yield an intact light chain and a portion of one heavy chain;

(2) Fab', the fragment of an antibody molecule can be obtained by treating whole antibody with pepsin, followed by reduction, to yield an intact light chain and a portion of the heavy chain; two Fab' fragments are obtained per antibody molecule;

(3) (Fab')2, the fragment of the antibody that can be obtained by treating whole antibody with the enzyme pepsin without subsequent reduction; F(ab')2 is a dimer of two Fab' fragments held together by two disulfide bonds;

(4) Fv, defined as a genetically engineered fragment containing the variable region of the light chain and the variable region of the heavy chain expressed as two chains; and (5) Single chain antibody ("SCA"), defined as a genetically engineered molecule containing the variable region of the light chain, the variable region of the heavy chain, linked by a suitable polypeptide linker as a genetically fused single chain molecule.

Methods of making these fragments are known in the art. (See for example, Harlow and Lane, Antibodies: A Laboratory Manual, Cold Spring Harbor Laboratory, N.Y. (1988), incorporated herein by reference).

As used in this invention, the term "epitope" means any antigenic determinant on an antigen to which the paratope of an antibody binds. Epitopic determinants usually consist of chemically active surface groupings of molecules such as amino acids or sugar side chains and usually have specific three dimensional structural characteristics, as well as specific charge characteristics.

Antibodies which bind to the Narp polypeptide of the invention can be prepared using an intact polypeptide or fragments containing small peptides of interest as the immunizing antigen. For example, it may be desirable to produce antibodies that specifically bind to the N- or C-terminal domains of Narp. The polypeptide or a peptide used to immunize an animal can be derived from translated cDNA or chemical synthesis which can be conjugated to a carrier protein, if desired. Such commonly used carriers which are chemically coupled to the peptide include keyhole limpet hemocyanin (KLH), thyroglobulin, bovine serum albumin (BSA), and tetanus toxoid. The coupled peptide is then used to immunize the animal (e.g., a mouse, a rat, or a rabbit).

If desired, polyclonal or monoclonal antibodies can be further purified, for example, by binding to and elution from a matrix to which the polypeptide or a peptide to which the antibodies were raised is bound. Those of skill in the art will know of various techniques common in the immunology arts for purification and/or concentration of polyclonal antibodies, as well as monoclonal antibodies (See for example, Coligan, et al., Unit 9, Current Protocols in Immunology, Wiley Interscience, 1994, incorporated by reference).

It is also possible to use the anti-idiotype technology to produce monoclonal antibodies which mimic an epitope. For example, an anti-idiotypic monoclonal antibody made to a first monoclonal antibody will have a binding domain in the hypervariable region which is the "image" of the epitope bound by the first monoclonal antibody.

The invention also provides a method for inducing the growth of a neuron by contacting the neuron with a growth inducing amount of Narp polypeptide or Narp encoding polynucleotide. As used herein, the term "growth" when referring to a neuron, refers to the neurite or dendrite promoting effect of Narp, rather than a mitotic event. The term includes growth of at least one dendrite. Preferably, the bioassay for determination of neurite outgrowth is the cortical explant assay described herein in Example 1, 12. Typically, the number of explants having neurite outgrowth (e.g., dendrites longer than about 10 cell diameters from the periphery of the explant) is counted and a population response is determined. Observation of migration of cells out of the explant is also observed by looking at the boundry of the explant to identify cells that have left the boundry. Such bioassays, as described herein, are useful not only for the identification of Narp and Narp fragments having activity, but also for identification of other pentraxins, for example, having "Narp-like" neurite outgrowth or neuronal migration activity. Further, the assays exemplified herein are useful across species, that is, a human pentraxin can be tested in a rat cell-based assay, and vice versa. Prior to the present invention, it was not known that pentraxins, which are now known to include Narp, possesed growth factor-like activities. Given the present teachings, one of skill in the art can now identify other pentraxins having similar growth promoting activities.

The term "contacting" refers to exposing the neuron to Narp so that the polypeptide can effectively induce neurite or dendritic outgrowth from the cell. Contacting may be in vitro, for example by adding Narp polypeptide to a tissue culture of neuronal cells or transfecting an expression vector containing an operable Narp-encoding polynucleotide to test for responsiveness of the neurons to Narp, for example. Detection of Narp activity can be observed by a dendritic outgrowth bioassay, as described above and in the present examples. As used herein, "growth inducing amount" refers to that amount of Narp which induces growth of at least one dendrite from a neuron. Contacting may be in vivo, for example by administering Narp polypeptide to a subject with a neuronal cell disorder, such as a neurodegenerative disease. Effective growth inducing concentrations of Narp polypeptide are from about 0.5 nM to 1.5 nM, and preferably from about 0.7 nM to 1.0 nM.

The Narp polypeptide is also useful for induction of neuronal cell migration. Narp polypeptide or polynucleotide, can be contacted with a neuronal cell, as described above for the method of inducing growth of the neuron, and for induction of migration of neurons. It may be desirable to induce migration of neurons in disorders such as Parkinson's disease or Huntington's disease after a neuronal cell grafting procedure, for example. Addition of Narp in such situations may provide support for neuronal cell growth and/or survival.

The invention also includes a method for the production of Narp polypeptide, in vitro. For example, a host cell containing an expression vector with Narp encoding polynucleotide (e.g., SEQ ID NO:1), is cultured under conditions which allow expression of the polynucleotide, and Narp polypeptide is isolated from the host cell. Preferably, the host cell is a mammalian cell, such as COS-1, thereby allowing production of a stable, active, glycosylated form of Narp polypeptide.

It may be desirable to contact a target cell component to detect Narp in a cell, for example for diagnostic purposes. The "target cell component" can be nucleic acid, such as DNA or RNA, or protein. For purposes of the invention, an antibody or nucleic acid probe specific for Narp may be used to detect the presence of Narp polypeptide (using antibody) or polynucleotide (using nucleic acid probe). Oligonucleotide primers based on any coding sequence region in the Narp sequence are useful for amplifying DNA, for example by PCR. The probes can be detectably labeled, for example, with a radioisotope, a fluorescent compound, a bioluminescent compound, a chemiluminescent compound, a metal chelator, or an enzyme. Those of ordinary skill in the art will know of other suitable labels for binding to the nucleic acid probe or antibody, or will be able to ascertain such, using routine experimentation. Any specimen containing a detectable amount of polynucleotide or antigen can be used. A preferred sample of this invention is tissue of the brain, e.g., cortex or hippocampus, or tissue of the testes or ovary. Preferably the subject is human.

The present invention also provides a method for treating a subject having or at risk of having a neuronal cell disorder associated with Narp. The method includes administering to the subject, a therapeutically effective amount of Narp polypeptide or Narp encoding polynucleotide. A subject "at risk of having a neuronal cell disorder" includes those patients at risk for stroke or familial related neuronal disorders (e.g., Huntington's disease).

"Therapeutically effective" as used herein, refers to that amount of Narp polypeptide or Narp polynucleotide encoding Narp, that is of sufficient quantity to ameliorate the cause of the neuronal cell disorder. "Ameliorate" refers to a lessening of the detrimental effect of the neuronal disorder in the patient receiving the therapy. The subject of the invention is preferably a human, however, it can be envisioned that any animal with a neuronal disorder can be treated in the method of the invention. Examples of neuronal cell disorders include but are not limited to Alzheimer's disease, Parkinson's disease, stroke, epilepsy, neurodegenerative disease, Huntington's disease, and brain or spinal cord injury/damage, including ischemic injury.

The invention also includes a method of treating a neuronal cell tumor having an etiology associated with Narp gene expression or Narp bioactivity, comprising administering to a subject with the disorder, a therapeutically effective amount of reagent which modulates Narp expression or bioactivity. In a neuronal cell tumor, Narp may be expressed in an altered manner as compared to expression in a normal cell, therefore it is possible to design appropriate therapeutic or diagnostic techniques directed to this sequence. The term "modulate" envisions increasing or decreasing the expression of Narp, depending on the indication, when a cell proliferative disorder, e.g., tumor, or neuronal cell disorder is associated with under- or overexpression of Narp polypeptide, respectively.

For example, a sense polynucleotide sequence (the DNA coding strand) encoding Narp polypeptide can be introduced into the cell to increase expression of a "normal" Narp gene. Other neuronal cell disorders associated with the expression of Narp can also be treated with nucleic acid sequences that interfere with Narp expression at the translational level. This approach utilizes, for example, antisense nucleic acid, ribozymes, or triplex agents to block transcription or translation of a specific Narp mRNA, either by masking that mRNA with an antisense nucleic acid or triplex agent, or by cleaving it with a ribozyme. Alternatively, the method includes administration of a reagent that mimics the action or effect of Narp or blocks the action of Narp. Therefore, when a neuronal tumor, for example a neuroblastoma, is etiologically linked with overexpression of Narp polynucleotide, is would be desirable to administer a Narp-inhibiting reagent such as an antisense polynucleotide.

Detection of elevated levels of Narp expression may be accomplished by hybridization of nucleic acids isolated from a cell suspected of having a Narp associated disorder with a Narp polynucleotide of the invention. Analysis, such as Northern Blot analysis, are utilized to quantitate expression of Narp. Other standard nucleic acid detection techniques or alternatively immunodiagnostic techniques for Narp polypeptides will be known to those of skill in the art (e.g., Western or Northwestern blot analysis).

Also included in the methods of treatment of neuronal cell disorders or tumors are peptidomimetic compounds based upon the amino acid sequence of the Narp polypeptide. Peptidomimetic compounds are synthetic compounds having a three-dimensional structure (i.e., a "peptide motif") based upon the three-dimensional structure of a selected peptide. The peptide motif provides the peptidomimetic compound with Narp agonist or antagonist activity that is substantially the same as, or greater than, the Narp agonist or antagonist activity of the peptide from which the peptidomimetic was derived. Peptidomimetic compounds can have additional characteristics that enhance their therapeutic application, e.g., enhanced cell permeability, increased receptor or polypeptide binding affinity and/or avidity, and prolonged biological half-life. The design of peptidomimetic compounds having agonist or antagonist activity can be aided through computer modeling techniques well known in the art. Other methods for the design, as well as the preparation of, peptidomimemtic compounds are well known in the art.

The present invention provides gene therapy for the treatment of a tumor or disease which is associated with Narp as discusses above. Such therapy would achieve its therapeutic effect by introduction of the appropriate Narp polynucleotide which contains a Narp gene (sense), into cells of subjects having the disorder. Delivery of sense Narp polynucleotide constructs can be achieved using a recombinant expression vector such as a chimeric virus or a colloidal dispersion system.

Gene therapy methods as described herein can be performed in vivo or ex vivo. In addition, it may be preferable to remove the majority of a tumor prior to gene therapy, for example surgically or by radiation.

Various viral vectors which can be utilized for gene therapy as taught herein include adenovirus, herpes virus, vaccinia, or, preferably, an RNA virus such as a retrovirus. Preferably, the retroviral vector is a derivative of a murine or avian retrovirus. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), and Rous Sarcoma Virus (RSV). Preferably, when the subject is a human, a vector such as the gibbon ape leukemia virus (GaLV) is utilized. A number of additional retroviral vectors can incorporate multiple genes. All of these vectors can transfer or incorporate a gene for a selectable marker so that transduced cells can be identified and generated. By inserting a Narp sequence (including promoter region) of interest into the viral vector, along with another gene which encodes the ligand for a receptor on a specific target cell, for example, the vector is now target specific. Preferred targeting is accomplished by using an antibody to target the retroviral vector. Those of skill in the art will know of, or can readily ascertain without undue experimentation, specific polynucleotide sequences which can be inserted into the retroviral genome, for example, to allow target specific delivery of the retroviral vector containing the Narp sense or antisense polynucleotide.

Since recombinant retroviruses are defective, they require assistance in order to produce infectious vector particles. This assistance can be provided, for example, by using helper cell lines that contain plasmids encoding all of the structural genes of the retrovirus under the control of regulatory sequences within the LTR. These plasmids are missing a nucleotide sequence which enables the packaging mechanism to recognize an RNA transcript for encapsidation. Helper cell lines which have deletions of the packaging signal include but are not limited to Ψ2, PA317 and PA12, for example. These cell lines produce empty virions, since no genome is packaged. If a retroviral vector is introduced into such cells in which the packaging signal is intact, but the structural genes are replaced by other genes of interest, the vector can be packaged and vector virion produced.

Another targeted delivery system for Narp polynucleotide, polypeptide or neurons containing Narp polynucleotide, is a colloidal dispersion system. Colloidal dispersion systems include macromolecule complexes, nanocapsules, microspheres, beads, and lipid-based systems including oil-in-water emulsions, micelles, mixed micelles, and liposomes. The preferred colloidal system of this invention is a liposome. Liposomes are artificial membrane vesicles which are useful as delivery vehicles in vitro and in vivo. It has been shown that large unilamellar vesicles (LUV), which range in size from 0.2–4.0 um can encapsulate a substantial percentage of an aqueous buffer containing large macromolecules. RNA, DNA and intact virions can be encapsulated within the aqueous interior and be delivered to cells in a biologically active form (Fraley, et al., *Trends Biochem. Sci.*, 6:77, 1981). In order for a liposome to be an efficient gene transfer vehicle, the following characteristics should be present: (1) encapsulation of the genes of interest at high efficiency while not compromising their biological activity; (2) preferential and substantial binding to a target cell in comparison to non-target cells; (3) delivery of the aqueous contents of the vesicle to the target cell cytoplasm at high efficiency; and (4) accurate and effective expression of genetic information (Mannino, et al., *Biotechniques*, 6:682, 1988).

Other means of encapsulating and delivering either Narp polypeptide or Narp-encoding polynucleotide (under expressable conditions) or transfected neurons containing Narp polynucleotide in operable linkage with regulatory elements for expression, will be known to those of skill in the art.

Antibodies or polynucleotides of the invention can be used in vitro and in vivo to treat and to monitor the course of amelioration of a Narp-associated disease in a subject or for diagnostic purposes. Thus, for example, by measuring the increase or decrease in the number of cells expressing antigen comprising a polypeptide of the invention or changes in the concentration of such antigen present in various body fluids (e.g., cerebrospinal fluid (CSF)) or in primary cortical cells, for example, it would be possible to determine whether a particular therapeutic regimen aimed at ameliorating the Narp-associated disease is effective.

Use of Narp polypeptide is useful for the in vitro survival of neurons for grafting into the central nervous system. The method of treating a subject with a neuronal disorder therefore includes intracerebral grafting of neurons to the region of the CNS having the disorder. Where necessary, the neuron can be genetically engineered to contain an exogenous gene. The disorder may be from either disease or trauma (injury). Neuronal transplantation, or "grafting" involves transplantation of cells into the central nervous system or into the ventricular cavities or subdurally onto the surface of a host brain. Such methods for grafting will be known to those skilled in the art and are described in *Neural Grafting in the Mammalian CNS*, Bjorklund and Stenevi, eds., (1985), and U.S. Pat. No. 5,082,670 incorporated by reference herein. Procedures include intraparenchymal transplantation, (i.e., within the host brain) achieved by injection or deposition of tissue within the host brain so as to be apposed to the brain parenchyma at the time of transplantation.

Administration of the neurons into selected regions of the recipient subject's brain may be made by drilling a hole and piercing the dura to permit the needle of a microsyringe to be inserted. The neurons can alternatively be injected intrathecally into the spinal cord region. The neuronal preparation permits grafting of neurons to any predetermined site in the brain or spinal cord, and allows multiple grafting simultaneously in several different sites using the same cell suspension and permits mixtures of cells from different anatomical regions. The present invention provides a method for transplanting various neural tissues, by providing previously unavailable neurons in order to grow a sufficient number of cells for in vitro gene transfer followed by in vivo implantation.

The neuron used for treatment of a neuronal disorder may optionally contain an exogenous gene, for example, an oncogene, a gene which encodes a receptor, or a gene which encodes a ligand, and/or a Narp-encoding polynucleotide. Such receptors include receptors which respond to dopamine, GABA, adrenaline, noradrenaline, serotonin, glutamate, acetylcholine and other neuropeptides, as described above. Examples of ligands which may provide a therapeutic effect in a neuronal disorder include dopamine, adrenaline, noradrenaline, acetylcholine, gamma-aminobutyric acid and serotonin. The diffusion and uptake of a required ligand after secretion by a donor neuroblast would be beneficial in a disorder where the subject's neural cell is defective in the production of such a gene product. A neuron genetically modified to secrete a neurotrophic factor, such as nerve growth factor, (NGF), or Narp might be used to prevent degeneration of cholinergic neurons that might otherwise die without treatment. Alternatively, neurons to be grafted into a subject with a disorder of the basal ganglia, such as Parkinson's disease, can be modified to contain an exogenous gene encoding Narp, and/or L-DOPA, the precursor to dopamine. Parkinson's disease is characterized by a loss of dopamine neurons in the substantia-nigra of the midbrain, which have the basal ganglia as their major target organ. Alternatively, neurons derived from substantia-nigra neuronal cells which produce dopamine could be introduced into a Parkinson's patient brain to provide cells which "naturally" produce dopamine.

Other neuronal disorders that can be treated similarly by the method of the invention include Alzheimer's disease, Huntington's disease, neuronal damage due to stroke, and damage in the spinal cord. Alzheimer's disease is characterized by degeneration of the cholinergic neurons of the basal forebrain. The neurotransmitter for these neurons is acetylcholine, which is necessary for their survival. Engraftment of cholinergic neurons, or neurons containing an exogenous gene for Narp which would promote survival of these neurons can be accomplished by the method of the invention, as described. Following a stroke, there is selective loss of cells in the CA1 of the hippocampus as well as cortical cell loss which may underlie cognitive function and memory loss in these patients. Once identified, molecules responsible for CA1 cell death can be inhibited by the methods of this invention. For example, antisense sequences, or a gene encoding an antagonist can be transferred to a neuron and implanted into the hippocampal region of the brain.

The method of treating a subject with a neuronal disorder also contemplates the grafting of neurons in combination with other therapeutic procedures useful in the treatment of disorders of the CNS. For example, the neurons can be co-administered with agents such as growth factors, gangliosides, antibiotics, neurotransmitters, neurohormones, neurotrophins, toxins, neurite promoting molecules and antimetabolites and precursors of these molecules such as the precursor of dopamine, L-DOPA.

The following examples are intended to illustrate but not limit the invention. While they are typical of those that might be used, other procedures known to those skilled in the art may alternatively be used.

EXAMPLE 1

MATERIALS AND METHODS

1. Animals and Supplies

Adult male rats Sprague-Dawley or Fischer-344 (LTP studies) were used in studies of Narp regulation. Developmental studies used male and female Sprague-Dawley pups of the indicated age. Radiochemicals were obtained from NEN-Dupont. All other reagents were from Fischer and Sigma unless specifically noted.

2. Construction and Screening of the Subtracted cDNA Library

A subtracted cDNA library was constructed as described (Yamagata, et al., supra, 1993). The subtracted library was screened with [$^{32}$P] cDNA prepared by reverse transcription of poly (A)+RNA prepared from hippocampus of control or seizure stimulated rats pretreated with cycloheximide (20 mg/kg i.p.) as described previously (Yamagata, et al., supra, 1993). Near full length cDNAs of rat Narp were isolated by iterative screening of an unsubtracted, oligo dT primed cDNA library prepared from hippocampus 4 hr after a maximal electroconclusive seizure (MECS).

3. DNA Sequencing

Both strands of 3 independent, near full length Narp cDNAs were sequenced as double-stranded plasmids with synthetic, specific primers using the dideoxynucleotide chain termination method with deoxyadenosine 5' [$\alpha$-$^{35}$S] thio triphosphate and Sequenase (USB).

4. Northern Analysis

This procedure was performed as described (Linzer and Nathans, *Proc Natl Acad Sci, USA*, 80:4271, 1983) with 10 $\mu$g of total RNA per lane. RNA was isolated by standard CsCl density centrifugation and assayed for yield and purity by UV spectroscopy. Gels were stained with ethidium bromide and the ribosomal bands visualized to assess equal loadings of RNA. The probe used for Northern analysis was a 1.8 kb 3' end fragment of Narp cDNA. The cDNA fragment was labeled by the random priming technique (Pharmacia) using [$\alpha$-32P] dCTP.

5. In situ Hybridization

Freshly dissected brain tissue was rapidly frozen in plastic molds placed on a dry ice/ethanol slurry as described previously (Cole et al., *Biochem*, 55:1920, 1990). Control and experimental tissues were frozen in the same tissue block to assure identical conditions during tissue sectioning, subsequent storage and in situ hybridization. [$^{35}$S]-labeled Narp antisense riboprobe was prepared from an appropriately restricted pBluescript plasmid containing the near full length CDNA. In situ hybridization was performed as described (Saffen, et al., *Proc Natl Acad Sci (USA)*, 85:7795, 1988). Selected slides were treated with photographic emulsion (Kodak NTB2) and counterstained as previously described (Jordan, C. A., Boca Raton, Fla., *CRC Press.*, 39, 1990). Semiquantitative analysis of autoradiographic images was performed using a computerized densitometer (Loats Associates; Westminister, Md.).

6. Electrophysiology

Seizures were induced in adult male Sprague-Dawley rats by maximal electroconvulsive seizure (MECS) using a constant current signal generator (ECT unit, Ugo Basil) as described previously (Cole et al., supra). For long-term potentiation (LTP) studies, Fischer-344 rats were implanted bilaterally with stimulating and recording electrodes in the perforant path and hilus of the dentate gyrus as described previously (Worley, et al., *Neurosci*, 13:4776, 1993). Rats were allowed to recover for at least 2 weeks before any recordings were performed. 12 chronically implanted rats received high-frequency (HF) stimulation in one hemisphere, and low-frequency (LF) stimulation in the other hemisphere. Electrical stimuli consisted of 200 msec diphasic, constant current pulses given at a stimulus intensity of 500 $\mu$A. The LF test stimulation was delivered at 0.1 Hz, and the HF stimulation parameters consisted of 50 repetitions of a 20 msec train (i.e., 8 pulses) delivered at 400 Hz (400 total pulses). All response data were digitized by computer at 20 kHz and stored on disk for subsequent off-line analysis. The field excitatory postsynaptic potential (EPSP) amplitude was measured as the voltage difference between two cursors set at the EPSP onset and 1 msec later. The HF parameters reliably induce LTP (Worley, et al., supra, 1993) and increases in EPSP amplitude, assayed 25 minutes after the stimulus, ranged from 20% to 30%. Following this treatment, the rats were sacrificed at either 30 min (n=6), 1 hr (n=2), 2 hrs (n=2), 4 hrs (n=2) or 24 hrs (n=2).

Three additional animals were pretreated with MK-801 (1 mg/kg, i.p.) 1 hr prior to the delivery of the HF stimulus. The intensity of the stimulus was adjusted such that the postsynaptic population response was identical to that prior to MK-801 administration. The MK-801 administration blocked LTP. Animals were sacrificed 2 hrs after the HF stimulus and processed for in situ hybridization.

7. Monocular Deprivation

Monocular deprivation was performed in adult Sprague-Dawley rats as described previously (Worley, et al., *Proc Natl Acad Sci, USA*, 88:5106, 1991) using an intravitreal injection of the sodium channel antagonist tetrodotoxin (TTX; 10 $\mu$l of 200 $\mu$M solution of TTX in PBS). To assess the effectiveness of TTX injections, its anticipated blockade of the consensual pupillary light reflex was monitored immediately after injection and prior to sacrifice. Identical treatment in the absence of TTX was performed in control rats.

8. In vitro Transcription and Translation

Narp protein was synthesized using in vitro transcription and translation (TNT) in a coupled reticulocyte lysate system (Promega). 1 $\mu$g of template DNA is used with rabbit reticulocyte lysate, TNT reaction buffer, amino acid mix (1 mM) minus methionine, [$^{35}$S]-methionine (1,000 Ci/mmol) at 10 mCi/ml, Rnasin ribonuclease inhibitor (40 U/ml), and T3 RNA polymerase (2 U/ml). BglI and KpnI were used to linearized the DNA plasmids. TNT reaction products were analyzed by SDS-PAGE. The polyacrylamide gels were first fixed in 10% (w/v) TCA, 10% (v/v) glacial acetic acid, and 30% (v/v) methanol followed by soaking in autoradiography enhancer (Fluoro-Hance, Research Product International) before the gels are dried and exposed to autoradiography.

9. Analysis of Post Translational Modification of Narp

TNT reactions are performed as described above except with the addition of 2.5 $\mu$g of dog microsomes (Promega). For the microsomal proteolytic protection assays, circular full-length Narp plasmid DNA (1 $\mu$g) or 5' truncated Narp plasmid DNA (1 $\mu$g) were used as the templates to synthesize full-length Narp protein (in the presence or absence of microsomes) or a 5' truncated Narp lacking the first 46 amino acids, respectively. Proteins were exposed to proteolytic digestion by trypsin (0.1 mg/ml), with or without Triton X-100 (0.1%). Reactions were analyzed by SDS-PAGE. Deglycosylation of Narp was performed by first adding SDS (0.5%) to the reticulocyte lysate and boiling for 2 min to lyse the microsomes. Glycosidase reactions were carried out at 37° C. overnight with endoglycosidase H (6 mU; Boehringer Mannheim) in reaction buffer (150 mM sodium acetate, pH 5.5).

10. Generation of Narp Polyclonal Antisera

The full length Narp cDNA sequence, exclusive of the putative signal sequence, was generated using PCR primers that encoded flanking restriction enzyme sequences (EcoRI, 5' primer and BamHI, 3' primer). The amplified Narp insert was subcloned in frame into pTrcHisA prokaryotic expression vector containing an amino-terminal hexahistidine (Invitrogen). Full length Narp protein was isolated and purified using the $Ni^{2+}$-agarose purification system (Qiagen). Eluted fractions were separated on preparative SDS-PAGE and the specific band excised from the gel. Approximately 1 mg of the recombinant Narp protein was used to immunize each rabbit (HRP; Denver, Pa.). The crude antisera specifically recognized the bacterial recombinant protein and the in vitro TNT product.

11. Metabolic Labeling of COS-1 cells and Immunoprecipitation of Narp

Full-length Narp cDNA insert was subcloned into a CMV-promoter containing mammalian expression construct (pRK5; Genentech). COS-1 cells are transiently transfected with 10 μg of plasmid DNA (vector alone and Narp expressing construct) using calcium phosphate method (Chen and Okayaman, *Molecular and Cellular Biology*, 7:2745, 1987). For metabolic labeling of COS-1 cells, 250 mCi/ml Trans [$^{35}$S] methionine (ICN) was added with a media change of 40 hrs after the initial transfection in Dulbecco's modified Eagle's medium (DMEM; Gibco) lacking methionine and supplemented with 1% fetal bovine serum (Hyclone) for 3 hr. Conditioned media were analyzed by SDS-PAGE and autoradiography.

Immunoprecipitation of Narp from the COS-1 cell conditioned media was performed as follows. Conditioned media were first cleared of cellular debris by centrifugation for 15 min at 1,500×g. Samples were adjusted to 1×Immunoprecipitation buffer [150 mM NaCl, 50 mM Tris-HCl, pH 7.4, 0.5% NP-40, 0.5% sodium deoxycholate, 5 mM EDTA, pepstain (50 μg/ml), leupeptin (50 μg/ml), aprotinin (10 μg/ml), and PMSF (0.25 mM) and precleared by mixing with 50 μl of protein A agarose (Pierce) for 30 min at 4° C. (Sisodia, et al., *Science*, 248:492, 1990). Secreted Narp was immunoprecipitated by mixing 3 μl of polyclonal Narp antisera with the conditioned media 4° C. for 6 hr. The immune complexes were collected by adding agar suspension in binding buffer (same as above) at 4° C. for 4 hours followed by subsequent washes with binding buffer. Narp was eluted in four 1 ml fractions with elution buffer. The yield of myc tagged Narp was determined by direct competitive ELISA (described below) and was typically ~250ng/10-cm dish.

12. Microexplant Cultures of the Cerebral Cortex

Cortices were dissected from P1 rat pups and dissociated into cortical explants by passing the tissue through a 24 gauge needle. Explants were washed twice with minimum essential medium (MEM; Gibco) supplemented with glucose (6 g/l) by sedimentation and resuspension in fresh media. The explants were then plated in 35-mm tissue culture dishes coated with poly-L-ornithine (Sigma). The tissue culture dishes were coated with 1 ml of poly-L-ornithine (0.1 mg/ml) overnight at room temperature and rinsed twice with $dH_2O$ before culturing explants in MEM with ~7–8 explants per dish in a 5% $CO_2$-humidified incubator at 37° C.

Transiently transfected COS-1 cells (with either pKR5 vector alone, pRK5 containing the full length Narp, or pRK containing a C-terminal myc-tagged Narp construct) were trypsinized and harvested 24 hr after transaction. Aggregates of COS-1 cells ($5 \times 10^5$ cells) were formed by inverted hanging drop cell culture (Kennedy, et al., *Cell*, 78:425, 1994) for 16–18 hr and transferred to cortical explant cultures. A single aggregate was added to each 35-mm dish. Co-cultures were maintained for 24 or 48 hrs and neurite outgrowth from each explant was examined and scored in triplicate dishes by an observer blind to the protocol. Explants that had neurite outgrowths and average length of at least 10–15 cell body lengths were scored as positive cortical explants. In other control experiments, the effect of co-culturing cortical explants with COS-1 cells expressing amyloid precursor protein-like protein (Slunt, et al., *J. Biol. Chem.*, 269:2637, 1994) from the mammalian expression vector CB6 was examined.

In other experiments, myc-tagged Narp was partially purified from COS-1 cell supernatant using agar column chromatography as described above, and examined for neurite outgrowth activity. The concentration of myc-Narp was quantitiated using a direct competitive ELISA described below. Differing concentrations of myc-Narp were added to culture dishes and the effects on neurite outgrowth examined.

Immunodepletion of myc-tagged Narp was performed by incubating partially purified myc-tagged Narp prepared from COS-1 cell conditioned media (~60 ng of Narp) with mouse anti-myc monoclonal antibody (0.5 μg, Oncogene) previously conjugated with protein G-agarose beads. The anti-myc protein G conjugate was prepared by incubating the antibody with 1 ml of gel slurry, (Pierce) for 2 hrs in IgG binding buffer (0.1M sodium acetate, pH 5.0) at 4° C. followed by centrifugation. The anti-myc protein G conjugate was then resuspended in buffer (0.15M NaCl, 0.05M Tris, pH 7.4) containing Narp and incubated overnight at 4° C. Control experiments substituted mouse fluid ascites (0.5 μg, Sigma) for the anti-myc Ab. The control immunodepletion experiment procedure was identical to the anti-myc Ab experiment.

13. Quantitiation of myc-tagged Narp using Direct Competitive ELISA

Myc-tagged Narp was quantitated using a standard antigen-inhibition curve generated with serial dilutions of a standard c-myc peptide (a.a. 412–418, Santa Cruz). Partially purified myc-tagged Narp was coated onto 96-well flat bottom, high binding plate (EIA/RIA, Costar) for 1 hour at room temperature. Wells were rinsed 3× with wash buffer (0.5% Surfact-Amps Tween 20, 1% Blocker BSA ion PBS, and 1 pack of BupH Dulbecco's PBS, Pierce) and blocked with blocking buffer (10% Blocker BSA in PBS, Pierce) for 30 minutes at room temperature. Primary mouse anti-myc antibody at 1000 ng/ml dilution (Oncogene Science) was preincubated with known amounts of c-myc peptide for 1 hour at room temperature before applying to wells coated with partially purified myc-tagged Narp. After 2 hours incubation at room temperature, the wells were rinsed 3× with wash buffer and goat anti-mouse IgG peroxidase conjugated antibody (1:1000, Pierce) was added for 1 hour at room temperature. ABTS [2,2'-Azinobis(3-ethylbenzothiazoline)-6 sulfonic acid diammonium salt reagent (Pierce)] was used as the peroxidase substrate solution and the hydrolysis was measured using an ELISA reader with 410-nm filter. Concentration of Narp was determined by calculating the amount of c-myc peptide necessary to competitively inhibit half maximal binding of anti-myc antibody to myc-Narp.

14. Immunohistochemistry

Cortical explants co-cultured with COS-1 cells from P1 rat pups were prepared as described above. Cultures were rinsed with Hank's Balanced Salt Solution (HBSS, Gibco, BRL) at 37° C., air dried for 20 min, and fixed with 3.7% formaldehyde in 10 mM sodium phosphate (PBS), pH 7.4 for 30 min at room temperature. Explants were blocked and permeabilized with a solution containing 0.5% Triton X-100, 10% normal blocking serum (Vector) in PBS for 4 hr at 4° C. and then incubated in primary antibodies; anti-microtubule-associated protein 2 mAb (MAP-2) at 1:1000 (SMI 52, Sternberger Monoclonals Incorporated), anti-tau mAb at 1:200 (Boehringer Mannheim) anti-glial fibrillary acidic protein mAb (GFAP) at 1:400 (Chemicon International Inc.), or control mouse ascities fluid at 1:200 (Sigma), overnight at 4° C. After rinsing off the primary antibodies, endogenous peroxidase was quenched by incubating with 1% $H_2O_2$ in PBS for 15 minutes at room temperature. Cultures were further incubated with biotinylated anti-mouse secondary antibody (50 μl/ml, Vector) in PBS for 1 hr at room temperature and immunoreactivity was visualized using the Vectastain Elite ABC and DAB substrate.

15. Interspecific Mouse Backcross Mapping

Interspecific backcross progeny were generated by mating (C57BL/6J×*M. spretus*)$F_1$ females and C57BL/6J males a s described (*Copeland and Jenkins, Trends in Genetics*, 7:113, 1991). A total of 205 $N_2$ mice were used to map the Narp locus. DNA isolation, restriction enzyme digestion, agarose gel electrophoresis, Southern blot transfer and hybridization were performed as described (Jenkins, et al., *Virol*, 43:26, 1982). All blots were prepared with Hybond-N$^+$ nylon membrane (Amersham). The probe, an ~500 bp EcoRI/BamHI fragment of rat cDNA corresponding to the 3' end of the ORF, was labeled with [$\alpha^{32}P$] dCTP using a nick translation labeling kit (Boehringer Mannheim); washing was done to a final stringency of 0.8×SSCP, 0.1% SDS, 65° C. A major fragment of 6.4 kb was detected in SphI digested C57BL/6J DNA and a fragment of 7.6 KB was detected in SphI digested M. spretus DNA. The presence or absence of the 7.6 kb *M. spretus*-specific SphI fragment was followed in backcross mice.

A description of the probes and RFLPs for the loci linked to Narp including erythropoietin (Epo) and platelet-derived growth factor alpha (PDGF) has been reported previously (Singh, et al., *Proc Nat Acad Sciences, USA*, 88:10706, 1991). One locus has not previously been reported for our interspecific backcross; FMS-like tyrosine kinase 3 (Flt3). The probe was an ~850 bp fragment of mouse cDNA that was kindly provided by Ihor Lemischka (Princeton, N.J.). The probe detected 11.5, 7.5 and 4.3 and 11.5, 7.5 6.0 and ~1.0 kb SphI fragments. The presence or absence of the 6.0 and ~1.0 kb M. spretus-specific SphI fragments, which co-segregated, was followed in backcross mice. Recombination distances were calculated as described (Green, New York, Oxford University press., 1981) using the computer program SPRETUS MADNESS. Gene order was determined by minimizing the number of recombination events required to explain the allele distribution patterns.

16. Sequence Analysis cDNA and amino acid sequences were analyzed using Geneworks (Intelligentics), Strider (Commissariat al'Energie Atomique, France), Protein predict (Rost and Sander, *Journal of Molecular Biology*, 232:584, 1993; Rost and Sander, *Proteins*, 19:55, 1994) and SBASE (Pongor et al., *Nucleic Acid Researh*, 22:3610, 1994).

EXAMPLE 2

NARP cDNA SEQUENCE

A novel cDNA corresponding to the 3' non-coding region of a ~2.5 kilobase (kb) mRNA was identified by differential screening of a subtracted CDNA library prepared from seizure stimulated hippocampus (Yamagata, et al., supra, 1993). A near full length cDNA was identified by iterative screening of an unsubtracted cDNA library prepared from hippocampus. The size of the cDNA (2561) corresponds closely to the estimated size of the mRNA determined by Northern analysis. The longest open reading frame (ORF) with an initiator methionine predicts a 432 amino acid protein. A second, independent clone (2460 bp which begins at nucleotide 101 of the longest clone) contains the entire ORF, and the nucleotide and the predicted amino acid sequences are identical to those of the longer clone. FIG. 1 shows the complete cDNA and deduced protein sequences. The initiator methionine was selected to be the best Kozak consensus for translation initiation and occurs at nucleotide 128 of the longest cDNA (Kozak, *J. Mol. Biol.*, 196:947, 1987). The ORF continues to the 5' end of the CDNA and there is no frame stop 5' to the predicted initiator methionine. Alternative initiator methionine are present at nucleotides 265, 271 and 466. The identified location of the translation start site is supported by analysis of the in vitro transcription/translation products (see below). The 3' non-coding region contains the ATTTA motif in positions 2362 and 2396 which may contribute to the rapid turnover of Narp mRNA (Shaw and Kamen, *Cell*, 46:659, 1986) and is present in many IEGs. No classical polyadenylation signal sequence (AATAAA) was identified; however, the sequence ATTAAA is present in 5 independent clones 21 nucleotides from the 3' terminal poly(A) tail.

FIG. 1 shows the nucleotide sequence of narp cdna and its predicted amino acid sequence. The last nucleotide of each line is numbered to the right. The translated protein sequence is shown below corresponding nucleotide sequence and is numbered on the left side. The putative signal peptide of 16 amino acids is underlined. A dot indicates the predicted first amino acid of the mature protein. Putative glycosylation sites are circled. Two putative ATTTA mRNA instability motifs are present in the 3'-untranslated region and are boxed. The putative polyadenylation signal (ATTAAA) is underlined.

EXAMPLE 3

PREDICTED PROTEIN SEQUENCE OF NARP; HOMOLOGY TO THE PENTRAXIN FAMILY

Narp has a calculated molecular weight of 46.2 kDa and a pI of 5.46. There is an amino terminal secretory signal peptide sequence (underlined in FIG. 1) predicted using methods from von Heijne (von Heijne, supra). The predicted cleavage site is between glycine and glutamine. Three potential N-linked glycosylation sites were identified (Geneworks program) at 133, 174 and 378 aa.

FIG. 2 shows a full-length amino acid sequences of rat CRP (Rassouli et al., supra) and SAP (Dowton and McGrew, supra) are shown with the corresponding homologous region of Narp. Identical amino acid residues are boxed. The eight amino acid "pentraxin family signature" is marked in boldface. The β-strand regions defined by X-ray crystallography of human SAP (Emsley et al., supra) are indicated by letter A–O and a single overline above the corresponding residues. Residues involved in calcium binding are indicated by a dot; Asp 58, Asn 59, Glu 136, Gln 137, Asp 138, and Gln 148. Conserved crysteine residues 36 and 95 are highlighted by an asterisk. Full length Narp is compared to guinea pig Apexin and human NPII. Regions that are identical in all three sequences are boxed while regions identical between two are shaded.

Narp is 24% and 26% identical to CRP and SAP, respectively, over a 210 amino acid span that includes the full length sequence of mature CRP and SAP and the carboxyl terminal 216 amino acids of Narp (Dowton and McGrew, Biochemical Journal, 270:553, 1990; Rassouli et al., *J. of Biological Chemistry*, 267:2947, 1992). FIG. 2A shows the alignment of Narp with rat CRP and SAP. Islands of homology are clustered throughout the sequence. Eight amino acids have been identified that constitute the "pentraxin family signature" sequence (H-X-C-X-S/T-W-X-S/T) (SEQ ID NO:8) which is present in all pentraxin family members (Breviaro, et al., *J. of Biological Chemistry*, 267:22190, 1992) and is also present in Narp.

The recent resolution of the crystal structure of SAP provides detailed structure-function information for the pentraxin family and identifies several functional domains (Emsley et al., *Nature*, 367:338, 1994). As isolated from ascites or pleural effusion fluids, SAP is a decameric molecule composed of identical subunits non-covalently associated in two pentameric rings that interact face to face. Each of the monomers contains 15 antiparallel β-strands (designated strands A through O; FIG. 2A) which form two β sheets. Corresponding regions of Narp are predicted to form β-strands (Rost and Sander, supra, 1993; Rost and Sander, supra, 1994). The pentraxin signature sequence corresponds to strand H. The region of Narp with highest homology to SAP/CRP spans the sequence between β-sheets K and L. This region of SAP is important in binding calcium (Emsley et al., supra). SAP binds two calcium ions with different affinities. The higher affinity binding site includes coordinating side chains of amino acids Asp 58, Asn 59, Glu 136, Asp 138 and the main chain carbonyl of Gln 137. All of these residues are present at homologous positions in Narp with the single exception that Narp encodes an Ala at homologous position 58 (FIG. 2A). Asp 58 is present in hamster SAP, human CRP and Limulus CRP but varies in CRPs from other species (Emsley et al., supra). The second calcium ion is coordinated by Glu 136, Asp 138 and Gln 148. Each of these residues is conserved in Narp. SAP binding to derivatized sugars involves the amide nitrogens of Gln 148 and Asn 59 which are oriented in the proper position to form hydrogen bonds with the sugar derivative via interactions of their amide oxygens with the calcium ions (Emsley et al., supra).

Cysteine residues Cys 36 and Cys 95 form a disulfide link between adjacent strands C and L and are present in most members of the pentraxin family (Emsley et al., supra). Cysteines are present in the homologous positions in Narp. Based on these homologies, we conclude that Narp is a member of the pentraxin family.

Computer modeling of the amino terminal 200 amino acids of Narp predicts that this region possesses a high degree (61%) of α-helical secondary structure (Rost and Sander, supra, 1993; Rost and Sander, supra, 1994). Helical wheel analysis (Cohen and Parry, *Science*, 263:488, 1994) of two of these putative helical domains (aa 40 to 82 and 105 to 132) indicates that they are strongly amphipathic with heptad repeats of hydrophobic amino acids.

Four additional novel pentraxins have recently been reported that are similar to Narp in that they exhibit the pentraxin consensus sequences in the carboxyl terminal half of the molecule but possess an extended N-terminal sequence that is novel. Information regarding the biochemistry and function of these molecules is limited and is based primarily on their sequence homology to SAP and CRP. TSG-14 is rapidly induced in endothelial cells by growth factor stimulation and is hypothesized to modify the extracelluar matrix of the endothelium (Breviaro, et al., supra; Lee et al., *J. Of Immunology*, 150:1804, 1993). Overall, TSG-14 is 22% identical to Narp but is similar to Narp in that it encodes ~200 amino acids N-terminal to the pentraxin homology region and this domain is predicted to possess a high degree of α-helical structure. Another pentraxin, termed NP (Neuronal Pentraxin) was purified from brain membranes as a binding protein for the sake venom toxin, taipoxin (Schlimgen et al., *Neuron*, 14:519, 1995). NP is similar in size to Narp and TSG-14 and its amino acid sequence is 45% identical to Narp. NP is expressed in discrete populations of neurons in the hippocampus, cortex and brain stem indicating a partially overlapping pattern of expression with Narp. The regulation of NP, particularly whether it is an IEG, has not been examined. NP potentiates the toxicity of taipoxin on glia and is hypothesized to play a role in reputake of extracellular proteins. The third novel pentraxin, termed Apexin, was purified and cloned independently by two groups from guinea pig sperm (Noland et al., *J. of Biological Chemistry*, 269:32607, 1994; Reid and Bloble, *Apexin, an acrosomal pentaxin*, 269:32615, 1994) The Apexin amino acid sequence is 90% identical to Narp and therefore Apexin may represent the guinea pig homologue of Narp (FIG. 2B). The nucleotide homology between Narp and Apexin continues beyond the end of the ORF into the 3' nontranslated sequence (82% identity in ORF, 25% identity in the 5' nontranslated sequence and 58% identity in the 3' nontranslated sequence). Apexin is expressed at high levels in the mature sperm acrosome and is hypothesized to play a role in protein aggregation during acrosome biogenesis.

It is notable that the reported Apexin cDNA is only 1572 nucleotides compared to the Narp cDNA which is 2561. The Apexin sequence appears to be full length since Northern analysis of Apexin identifies a prominent band of 1.6 kb in testis (brain RNA was not examined) (Reid and Blobel, supra) which is consistent with the size of their reported cDNA. The Northern blot herein (see below) indicates that the Narp mRNA transcript is enriched in brain relative to testis but does not yield a conclusive comparison of transcript size. Accordingly, the difference in transcript size between Narp and Apexin could be due to differences in species or tissue specific expression. The fourth novel pentraxin, termed NPII (FIG. 2B; also termed NPTX2), is a human genomic clone that was identified by a low stringency screen with NP (Hsu and Perin, *Genomics*, 28:220, 1995). Consistent with its possible regulation as an IEG, it is noted that the putative promoter region of NPII possesses consensus bonding sites for the transcription factors CRE and Zif268.

EXAMPLE 4

NARP mRNA IS ENRICHED IN BRAIN AND IS RAPIDLY INDUCED BY SEIZURE

The expression of Narp mRNA was examined by Northern blot analysis of total RNA from rat cerebral cortex, hippocampus, and different peripheral tissues. Narp mRNA was also assayed in hippocampus and cortex following MECS.

Narp is enriched in cortex and hippocampus relative to peripheral tissues. Lower levels of Narp mRNA were also detected in the testis (and ovary). Narp mRNA is induced in the hippocampus within 1 hour following MECS and remains elevated for as long as 8 hrs. Densitometry of the autoradiogram indicates that Narp mRNA is induced at least 5-fold by MECS. Increased levels of mRNA in the hippocampus following MECS are associated primarily with granule cell neurons.

Rats were chronically implanted for in vivo recording and were stimulated as described in Methods. Narp mRNA was analyzed by in situ hybridization. The upper brain is from a rat that received a unilateral high frequency LTP stimulus to the right perforant path and an identical number of low frequency stimuli to the left hippocampus 4 hr prior to sacrifice. Narp mRNA was markedly increased in the granule cell layer that received the LTP stimulus. The lower brain is a composite of half brains from a naive control rat (left side) and a rat that received a MECS seizure 4 hrs prior to sacrifice (right side). MECS results in Narp mRNA induction in the superficial and deep layers of the neo- and pyriform cortices as well as the dentate gyrus.

Densitometry of the autoradiographic image indicated a 2.5 fold increase in the grain density over the granule cell layer of the dentate gyrus in the 4 hr LTP hippocampus compared to control.

Narp mRNA is induced in animals pretreated with cycloheximide indicating that the induction does not require new protein synthesis (data not shown). mRNA induction in the absence of new protein synthesis is a defining characteristic of IEGs (Lau and Nathans, *Proc Nat Acad Science, USA*, 84:1182, 1987).

EXAMPLE 5

NARP IS RAPIDLY REGULATED BY PHYSIOLOGICAL SYNAPTIC ACTIVITY

The regulation of Narp mRNA was also analyzed using the paradigm of in vivo long-term potentiation (LTP). Postnatal day 21 rat received a monocular injection of tetrodotoxin 4 hr prior to sacrifice. In situ analysis of Narp mRNA demonstrated reduced expression in the differentiated visual cortex. A prominent difference in expression is evident between contiguous primary and association visual cortices (boundary is indicated by the lateral error) while in control cortex, Narp mRNA expression is uniform across this boundary. Densitometry of the autoradiographic image indicates a 1.8 fold higher grain density over the temporal cortex relative to the contiguous deprived visual cortex. Identical results were observed in 4 additional 21 day old rats and 3 adult rats sacrificed 4 hrs after TTX injection.

Narp mRNA is strongly induced 4 hrs after a high-frequency synaptic stimulus (HF) that produces LTP (n=2). The time course of Narp mRNA increases following LTP induction was also assayed. Increases in Narp mRNA were detected as early as 30 min (n=6), appeared near maximal after 1 hr (n=2), 2 hrs (n=2), and 4 hrs (n=2) and returned to basal level after 24 hrs (n=2). This time course is similar to that following MECS (Example 4). Induction of Narp mRNA following LTP is dependent on the activation of N-methyl D-aspartate (NMDA) receptors since prior treatment of rats with the non-competitive NMDA receptor antagonist, MK-801 (1 mg/kg, i.p.), blocked both increases in Narp mRNA and LTP (n=3).

Narp mRNA is readily detected by in situ hybridization in normal cortex and is enriched in cortical layers 2/3 and 5/6. To determine if this basal expression is regulated by synaptic activity, we monitored Narp mRNA levels in visual cortex following monocular injection of tetrodotoxin (TTX). This manipulation reduces afferent activity (Worley, et al., supra, 1991). Rapid response genes whose expression is dynamically regulated to the contralateral visual cortex and results in a rapid decrease in the expression of several of the IEGs known to be expressed in cortex indicating that their basal expression is continuously maintained by natural afferent synaptic activity in this paradigm include zif268 (Worley et al., *Cold Springs Harbor Symposium on Quantitative biology*, 55:213, 1990; Worley et al., supra, 1991), prostaglandin synthase (Yamagata et al., supra, 1993), Egr-3 (Yamagata et al., supra, 1994), Arc (Lyford et al., supra) and 6A activin (Andreasson and Worley, supra). Because there are no intercranial manipulations and because the perturbation results in a reduction of natural activity rather than a stimulation of activity, as results with MECS and in vivo LTP, dynamic regulation in this monocular deprivation paradigm provides some of the strongest evidence of a role for the gene in normal synaptic physiology.

Narp mRNA is reduced in the deafferented visual cortex, most noticeably in cortical layers 2/3, within 4 hrs. after TTX injection. The reduction of Narp mRNA is most evident in comparisons of the contiguous association cortex and primary visual cortex where there is a prominent reduction of hybridization. In control cortex, the level of hybridization is uniform across this same boundary region. Because visual projections in the rodent are ~90% crossed (Zilles et al., *J. of Comparative neurology*, 226:391, 1984), the effect of monocular deprivation is almost exclusively contralateral. The effect of monocular TTX injection on basal expression of Narp mRNA is less dramatic than is evident with certain other IEGs such as zif268. This difference in the degree of reduction of Narp and zif268 mRNAs does not appear to be due to a slower rate of degradation of Narp since similar difference in the degree of mRNA reduction were also observed 18 hrs following TTX injection (n=5). Narp mRNA in cortex is less abundant than zif268 and technical differences in detection may contribute to their differential responsiveness. Alternatively, basal expression of Narp in cortex may be regulated by signals in additional to those generated by afferent activity.

EXAMPLE 6

NARP mRNA EXPRESSION IS DEVELOPMENTALLY REGULATED AND ENRICHED IN LIMBIC STRUCTURES AND SENSORY GANGLIA

The developmental expression of Narp mRNA was assayed by northern blot analysis of total RNA isolated from whole brains of embryonic day 14 to adult. Northern analysis was done for total RNA (10 µg/lane) prepared from forebrains of embryonic days 14, 15, 17, 19, 21, and postnatal days 1,4,8,12,16,5 wks, 8 wks, and 3 months old rats. Narp mRNA is detected as early as embryonic day 14 and increases steadily to peak levels between postnatal days 16 and 21.

Narp mRNA was first detected at embryonic day 14 and increased monotonically to peak levels at postnatal day 21. Levels remain high in adult animals. In situ hybridization was used to examine the anatomical distribution of Narp mRNA in embryonic day 19 rats. In situ analysis of expression of Narp mRNA in embryonic day 19 rat forebrain (magnification 5x). Narp mRNA is detected in the hippocampus (h), habenula (b), ventromedial hypothalamus (v), and the trigeminal ganglia (t). Narp mRNA is detected in the habenula, dorsal medial hypothalamus, hippocampus and trigeminal ganglia. Lower levels are present in cortex and other forebrain structures.

EXAMPLE 7

IN VITRO SYNTHESIS AND POST TRANSLATIONAL MODIFICATION OF NARP

In vitro transcription/translation (TNT) was used to confirm the predicted ORF. Circular and linearized Narp cDNA plasmids cloned in pBluescript SK+ vector, were used as templates to synthesis Narp protein by in vitro transcription and translation (TNT). Translated [$^{35}$S]-labeled products are analyzed by SDS-PAGE. A ~46 kDa protein product as detected using the circular or linearized full-length Narp plasmids. A ~43 kDa protein is synthesized from a plasmid, 5' truncated Narp, that lacks the putative initiator methionine but includes the first internal methionine. The observed product size is consistent with translation initiation from the first internal methionine. No product wass detected in the absence of added DNA (dH$_2$O control). The longest cDNA clone produced a protein with an apparent m.w. of ~46 kDa, which is identical to the predicted size. TNT using a cDNA clone that begins ~30 nucleotides 3' to the predicted initiator methionine produced a ~43 kDa protein (5' truncated Narp), which corresponds to the predicted product size synthesized from the first internal methionine. Restriction of the same CDNA prior to TNT with BglI, which cuts 67 nucleotides 5' to the carboxyl terminus of the predicted ORF (nucleotide 1242), results in a product of reduced size consistent with the position of the restriction site in the ORF. These experiments support the predicted ORF.

The ORF of Narp encodes a putative secretory signal peptide. To assess the presence of a functional signal sequence, full length Narp was prepared by TNT in the presence of dog microsomes. The microsome preparation has the necessary activity to translocate the nascent protein into the microsome and cleaves the signal sequence. Full-length Narp was synthesized by in vitro TNT reactions in the presence or absence of dog microsomes (DM). Translation was more efficient in the presence of microsomes and nonspecific bands at ~34 and ~27 kDa are not evident. A slight reduction in the size of the Narp protein was detected compared to the Narp protein synthesized in the absence of dog microsomes, consistent with cleavage of the signal sequence.

Narp prepared in the presence of dog microsomes yields several products that migrate on SDS-PAGE with an apparent molecular weight of ~44 to ~58 kDa. The ~44 kDa product is slightly smaller than the ~46 kDa product prepared without microsomes consistent with microsome-dependant signal peptide cleavage. Demonstration that Narp is secreted by COS-1 cells (below) is also consistent with the hypothesis that Narp possesses a functional signal sequence.

Narp has three potential N-glycosylation sites.

Other pentraxins are known to by glycosylated and this modification may be important in their saccharide binding properties (Emsley et al., supra). In addition to the product that migrates slightly faster than Narp prepared without microsomes described above (~44 kDa), a second product is observed that migrates with an apparent m.w. ~58 kDa. To determine if mature Narp is glycosylated, we examined the effect of treating the TNT/ microsome product with endoglycosidase H. Endoglycosidase H converted the ~58 kDa-band to a ~44 kDa product consistent with the interpretation that the ~58 kDa band is glycosylated Narp.

EXAMPLE 8

NARP PROTEIN IS SECRETED

COS-1 cells were transiently transfected with pRK5Narp or vector alone. 40 hrs after transfection, cells were metabolically labeled with [$^{35}$S]-methionine 3 hrs prior to sampling media. Conditioned media from cells was analyzed by SDS-PAGE and autoradiography. A prominent band of ~58 kDa is present in the media of cells transfected with pRK5Narp that is not present in cells transfected with vector alone. COS-1 cells were transiently transfected with 10 µg of plasmid DNA (pRK5 vector alone or pRK5Narp). 40 hrs after transfection, COS-1 cells ere labeled with 250 µCi/ml [$^{35}$S] methionine for 3 h in Met$^-$ DMEM supplemented with 1% dialyzed fetal bovine serum.

Supernatants from pRK5 vector alone and pRK5Narp were collected and fractionated on SDS-polyacrylamide gels. A ~58 kDa band expressed only by COS-1 cells transfected with PRK5Narp was observed, suggesting that Narp was secreted into the media. The ~58 kDa band is enriched in the media and was not detected in the pelleted COS-1 cells. To confirm that the ~58 kDa band represented Narp, immunoprecipitations were performed from the conditioned media using a polyclonal rabbit antisera generated against a full length Narp bacterial fusion protein and demonstrated that the ~58 kDa band selectively precipitated. These data strongly suggest that Narp is secreted into the media by the transfected COS-1 cells. It is unlikely that Narp is passively released into the media by COS-1 cells that are injured or dying, unlikely since the metabolic label, which is incorporated into newly synthesized protein, is added 40 hrs after transfection at a time when cytoxic effects of this manipulation should be resolved. Additionally, media was sampled 3 hours after addition of the metabolic label, thereby limiting the interval during which cells might undergo spontaneous cell death and release of intracellular contents.

EXAMPLE 9

BIOCHEMICAL STUDIES OF NARP; DEMONSTRATION OF CALCIUM-DEPENDENT BINDING TO A COMPLEX SACCHARIDE MATRIX

Pentraxins bind specifically to derivatized saccharides and this lectin property is thought to be essential for their biological function (Emsley et al., supra). The close homology of Narp to other pentraxins, particularly at the Ca$^{2+}$ and carbohydrate binding domains, suggests that Narp may also function as an endogenous lectin. Substrates typically used in pentraxin binding assays are modified agar. Agar is a polysaccharide that contains agarobiose, sulfate, and pyruvate (Hind et al., *J. Exp. Med.*, 159:1058, 1984) and agarose is prepared from agar by removing sulfated sugars. The polysaccharide backbone of agarose (marketed under trade name sepharose) can be derivatized by covalent attachment to a variety of molecules. CRP and SAP are known to bind to phosphatidylethanolamine-sepharose (PE-sepharose) and phosphatidylcholine-sepharose (PC-sepharose) and these substrates are commonly used to purify CRP and SAP from body fluids (Schwalbe et al., *Biochemistry*, 31:4907, 1992). In all cases, binding to these substrates is calcium dependent. To examine the hypothesis that Narp is a calcium-dependent lectin, a full length C-terminal myc-tagged Narp expression construct was prepared in pRK5 and expressed in COS-1 cells for binding studies. The COS-1 cell-derived myc-tagged Narp is biologically active in the neurite outgrowth assay described below and was used in preference to native Narp because of the relative insensitivity of the Narp antisera for immunoblots.

myc-tagged Narp binds specifically to agar in the presence of Ca$^{2+}$ and quantitatively elutes in the presence of divalent cationic chelator, EDTA. The estimated size of the EDTA elutable band is ~60 kDa and corresponds closely to the size of the glycosylated Narp prepared by TNT with dog microsomes. No EDTA elutable band was detected in parallel experiments that used conditioned media from COS-1 cells transfected with the expression vector lacking the Narp insert. Myc-tagged Narp did not bind in a calcium-dependent manner to agarose, low melting agarose, PC-sepharose or PC-sepharose, indicating that the substrate specificity of Narp is distinct from either CRP or SAP. The difference in binding to agar and agarose suggests that the pyruvate or sulfated side chains present in agar may be important in binding to Narp.

EXAMPLE 10

NARP PROMOTES NEURITE OUTGROWTH OF CORTICAL EXPLANT NEURONS

Pentraxins possess structural and biochemical similarities to the class of calcium-dependent plant-derived lectins which include concanavili A (Emsley et al., supra). Concanavalin A produces marked effects on a variety of cell types including neurons (Lin and Levitan, *Science*, 237:648, 1987; Lin and Levitan, *Trends in Neuroscience*, 14:273, 1991) and we have examined the possibility that Narp may mimic certain of these effects. Concanavalin A is highly active in promoting neurite outgrowth (Lin and Levitan, supra, 1987). Accordingly, we examined the possibility that Narp might also promote neurite outgrowth.

Cortical explants were prepared from postnatal day 1 rat pups as described. One day after plating cortical explants, COS-1 cells, which had previously been transfected with either a Narp expression construct or the vector alone, were added to the culture. In co-cultures expressing Narp, cells at the periphery of the explant exhibited exuberant outgrowth of processes within 24 hours of the addition of the COS-1 cells. Process outgrowth was observed surrounding the perimeter of each of 26 separate explants from 3 dishes in co-cultures that expressed Narp, while explant cultured with control COS-1 cells (17 separate explants from 3 dishes) or without COS-1 cells (16 explants from three dishes) exhibited no processes. By 48 hours in co-culture with Narp, processes were longer and more prominent than at 24 hrs and isolated cells with enlogated processes were seen surrounding the explant which appeared to have migrated out of the body of the explant. In control co-cultures, only infrequent short processes were present by 48 hrs without evidence of cellular migration. Similar results were obtained in 4 additional experiments. As a control for the specificity of Narp in this assay, the effect of co-culturing cortical explants with COS-1 cells that express and secrete amyloid precursor protein-like protein (APLP-2)(Slunt et al., supra) was examined. These explants appeared identical to control explants cultures either without COS-1 cells or with COS-1 cells transfected with vector alone.

To determine the cellular composition of the Narp-dependent process outgrowth, we performed immunohistochemistry using antisera for the neuron specific proteins MAP2 (Pennypacker et al., *Experimental Neurology*, 111:25, 1991), which is selectively expressed in neuronal dendrites, and tau, which is expressed in neuronal axons (Binder et al., *J. of Cell Biology*, 101:1371, 1985), as well as for the glial specific protein, glial fibrillary acidic protein (GFAP)(Rinaman et al., *J. of Neuroscience*, 13:685, 1993). Cortical explants prepared from postnatal day 1 rat pups were co-cultured for 48 hrs with COS-1 cells that had previously been transfected with a Narp expression construct or the vector alone (Control) as described in method. Cultures were stained with the neuron specific anti-MAP2 mAb. In explants co-cultured with control COS-1 cells, MAP2 positive cells are largely restricted to the body of the explant. By contrast, exuberant MAP2 positive neurite outgrowth is evident from the cortical explants co-cultured with COS-1 cells expressing Narp. MAP2 positive cell bodies are visualized beyond the edge of the explant suggesting migration from the explant. Magnification was 400×.

In control explants, MAP2 positive cell bodies and processes were present within the explant and few processes are seen extending beyond the edge of the explant. By contrast, explants co-cultured with Narp secreting COS-1 exhibited MAP2 positive cells with exuberant processes both at the border of the explant and extending many cell body diameters from the edge of the explant. The morphology and immunohistochemical properties of these cells indicate that they are neurons. Tau immunostaining was difficult to detect in control explants and was not increased in explants co-cultured with Narp secreting COS-1 cells. GFAP stained glial cells appeared to be largely restricted to the body of the explant at the 24 hr and 48 hr time points. Narp secreting COS-1 cells promote neurite outgrowth and migration of neurons from the cortical explant. This effect is not accompanied by prominent growth or migration of glial suggesting that the effect is primarily on neurons.

The neurite outgrowth promoting effect of Narp was used as a bioassay of its function to test the activity of C-terminal myc-tagged Narp. Cortical microexplants grown in co-culture with COS-1 cells expressing myc-Narp demonstrated the same growth of neurites and migration of neurons as explants co-cultured with COS-1 cells secreting natural Narp. We conclude that the myc epitope tag does not interfere with the biological activity of Narp in this assay.

Using the COS-1 cell-generated myc-Narp, two additional sets of experiments were performed to confirm that the active principle in the co-culture paradigm is Narp. In the first set of experiments, agar column chromatography was used to prepare partially purified myc-tagged Narp. Addition of this material to the microexplant culture reproduced the neurite outgrowth effect of co-culture with Narp secreting COS-1 cells. In control experiments, identical agar column fractions prepared from COS-1 cells transfected with the pRK5 vector alone did not induce neurite outgrowth. Partially purified myc Narp induces neurite outgrowth.

Cortical explants from postnatal day 1 rat pups were cultured on poly-L-ornithine coated plates. myc-tagged Narp was partially purified from COS-1 cell supernatant and aliquots were added to culture media. The amount of myc-tagged Narp was determined by ELISA. After 24 hrs, the number of explants with neurite outgrowth was determined and expressed as the percent of the total number of cortical explants. Data are from three separate experiments each performed in duplicate. Neurite outgrowth is observed with ~40 ng/ml of Narp. Control experiments used identical volumes of agar column fractions prepared from conditioned media of COS-1 cells transfected with vector alone. Explants treated with the control fractions demonstrate a 20–30% spontaneous outgrowth.

The second set of experiments used a myc monoclonal antisera to immunodeplete myc-tagged Narp from the agar column eluate. Addition of myc monoclonal antibody and subsequent precipitation with protein G sepharose, removed neurite outgrowth promoting activity. In control experiments, addition of mouse ascites fluid followed by protein G precipitation did not block this activity.

Partially purified myc-tagged Narp (~50 ng in 200 $\mu$l) was immunodepleted using mouse anti-myc antibody conjugated to protein G-agarose beads. Control experiments substituted mouse ascites for anti-myc antibody. Immunodepleted and control fractions were added to media and neurite outgrowth was assayed after 24 hrs. Data are from two separate experiments each performed in quadruplicate.

In the final set of experiments, the concentration of Narp necessary to promote outgrowth was examined. Again, we utilized myc-tagged Narp and established a direct competitive ELISA. Aliquots of agar column fractions were assayed in parallel for biological activity and levels of myc-tagged Narp were quantitated. The studies indicated that full activity is produced by ~40 ng/ml of myc Narp. Based on the estimated molecular weight of the Narp monomer (~58 kDa), this translates to an effective concentration of ~0.8 nM. Higher concentrations were without additional effect.

In conjunction, these experiments establish that Narp promotes dendritic neurite outgrowth and establishes the concentration range of its activity to be comparable to that of growth factor-induced effects in other systems.

EXAMPLE 11

CHROMOSOMAL LOCALIZATION OF NARP

The mouse chromosomal location of Narp was determined by interspecific backcross analysis using progeny derived from matings for [(C57BL/6J×Mus spretus) $F_1$×C57BL/6J] mice. The mapping results indicate that Narp is located in the distal region of mouse chromosome 5 linked to Epo, Pdgfa and Flt3. Although 159 mice were typed for every marker, up to 191 mice were typed for some pairs of markers. Each locus was analyzed pairwise combinations for recombination frequencies using the additional data. The ratios of the total number of mice exhibiting recombinant chromosomes to the total number of mice analyzed for each pair of loci and the most likely gene order are: centromere-Epo-7/191-Pdgfa-3/177-Flt3-0/160-Narp. The recombination frequencies [expressed as genetic distances in centi-Morgans (cM) +/− the standard error] are -Epo-3.7+/−1.4-Pdgfa-1.7+/−1.0-[flt3, Narp]. No recombinations were detected between Flt3 and Narp in 160 animals typed in common suggesting that the two loci are within 1.9 cM of each other (95% confidence limit).

We have compared our interspecific map of chromosome 5 with a composite mouse linkage map that reports the map location of many uncloned mouse mutations. Narp mapped in a region of the composite map that lacks mouse mutations with a phenotype that might be expected for an alteration in this locus.

The distal region of mouse chromosome 5 shares a region of homology with a human chromosome 7 and 13.

Although the invention has been described with reference to the presently preferred embodiment, it should be understood that various modifications can be made without departing from the spirit of the invention. Accordingly, the invention is limited only by the following claims.

What is claimed is:

1. An isolated polynucleotide encoding a Narp polypeptide wherein the amino acid sequence of the polypeptide is set forth in SEQ ID NO:2.

2. The isolated polynucleotide of claim 1, wherein the Narp nucleotide sequence is set forth in SEQ ID NO:1 (FIG. 1), and in SEQ ID NO:1 wherein T can also be U.

3. A recombinant expression vector comprising a polynucleotide according to claim 1.

4. The vector of claim 3, wherein the vector is a plasmid.

5. The vector of claim 3, wherein the vector is a virus.

6. An isolated host cell stably transformed with the vector of claim 3.

7. A method for producing a neuronal cell growth factor comprising culturing host cells of claim 6 under conditions which allow expression of the polynucleotide sequence and isolating the growth factor.

* * * * *

SEQUENCE LISTING

<160> NUMBER OF SEQ ID NOS: 8

<210> SEQ ID NO 1
<211> LENGTH: 2569
<212> TYPE: DNA
<213> ORGANISM: ARTIFICIAL
<220> FEATURE:
<223> OTHER INFORMATION: Narp cDNA
<221> NAME/KEY: CDS
<222> LOCATION: (128)..(1423)

<400> SEQUENCE: 1

```
tggtgctggc gtttccctgc ttgcacgcgg ttccctcgag cgccgctccg accgacgtag      60
ccggccgcga aggcgcccag acggcaagcc agcgacccat gctgaagtga gcgcccaggt     120 cagcgag atg ctg gcg ctg ctg acc gcc ggc gtg gcg ctc gcc gtg gcc      169
        Met Leu Ala Leu Leu Thr Ala Gly Val Ala Leu Ala Val Ala
        1               5                   10 gcg gga caa gcc cag gat aac ccg ata cct ggc agt cgc ttc gtg tgc      217
Ala Gly Gln Ala Gln Asp Asn Pro Ile Pro Gly Ser Arg Phe Val Cys
15                  20                  25                  30 acc gcg ctg ccc ccc gaa gcg gcg cgc gcc ggc tgc ccg ctg ccc gcg      265
Thr Ala Leu Pro Pro Glu Ala Ala Arg Ala Gly Cys Pro Leu Pro Ala
                35                  40                  45 atg ccc atg cag gga ggc gcg ctg agc cct gag gag gag ctg cga gcc      313
Met Pro Met Gln Gly Gly Ala Leu Ser Pro Glu Glu Glu Leu Arg Ala
            50                  55                  60 gct gtg ctg cac tgg cgc gag acc gtc gtg cag cag aag gag acg ctg      361
Ala Val Leu His Trp Arg Glu Thr Val Val Gln Gln Lys Glu Thr Leu
        65                  70                  75 ggc gct cag cga gaa gcc atc cga gaa ctc acc agc aag ctg gcc cgc      409
Gly Ala Gln Arg Glu Ala Ile Arg Glu Leu Thr Ser Lys Leu Ala Arg
    80                  85                  90
```

```
tgt gag gga cta gcc ggc ggt aag gcg cgc ggc acg ggg gcc acg ggc    457
Cys Glu Gly Leu Ala Gly Gly Lys Ala Arg Gly Thr Gly Ala Thr Gly
 95             100                 105                 110 aag gac acc atg ggc gac ctg ccg cgg gac ccg ggc cac gtc gtg gag    505
Lys Asp Thr Met Gly Asp Leu Pro Arg Asp Pro Gly His Val Val Glu
            115                 120                 125 cag ctt agc cgc tcg ctg cag acc ctc aag gac cgc ttg gag agc ctc    553
Gln Leu Ser Arg Ser Leu Gln Thr Leu Lys Asp Arg Leu Glu Ser Leu
        130                 135                 140 gag ctc caa ctc cac acc aac gcg tct aat gcc ggg ctg ccg agc gac    601
Glu Leu Gln Leu His Thr Asn Ala Ser Asn Ala Gly Leu Pro Ser Asp
    145                 150                 155 ttc cga gag gtg ctc cag cgg agg ctg ggg gag ctg gag agg cag ttg    649
Phe Arg Glu Val Leu Gln Arg Arg Leu Gly Glu Leu Glu Arg Gln Leu
160                 165                 170 cta cgc aag gtg gcc gag ctg gaa gac gag aag tcc ctg ctc cac aat    697
Leu Arg Lys Val Ala Glu Leu Glu Asp Glu Lys Ser Leu Leu His Asn
175                 180                 185                 190 gag acc tcg gct cac cgg cag aag aca gag aac aca ctg aat gca ctg    745
Glu Thr Ser Ala His Arg Gln Lys Thr Glu Asn Thr Leu Asn Ala Leu
                195                 200                 205 ctg cag agg gtg act gag ctg gag aga ggc aac agt gca ttc aag tca    793
Leu Gln Arg Val Thr Glu Leu Glu Arg Gly Asn Ser Ala Phe Lys Ser
            210                 215                 220 cca gat gca ttc aaa gtg tcc ctc cct ctc cgt aca aac tac cta tac    841
Pro Asp Ala Phe Lys Val Ser Leu Pro Leu Arg Thr Asn Tyr Leu Tyr
        225                 230                 235 ggc aag atc aag aag acg ttg ccc gag ctg tat gcc ttc acc atc tgc    889
Gly Lys Ile Lys Lys Thr Leu Pro Glu Leu Tyr Ala Phe Thr Ile Cys
    240                 245                 250 ctg tgg ctg cgg tcc agc gcc tcg cca ggc atc ggc acg cca ttc tcc    937
Leu Trp Leu Arg Ser Ser Ala Ser Pro Gly Ile Gly Thr Pro Phe Ser
255                 260                 265                 270 tac gct gtg cct ggg caa gcc aat gag att gtg ctg ata gag tgg ggt    985
Tyr Ala Val Pro Gly Gln Ala Asn Glu Ile Val Leu Ile Glu Trp Gly
                275                 280                 285 aac aat ccc ata gag ctg ctt atc aac gac aag gtc gca cag ctg ccc   1033
Asn Asn Pro Ile Glu Leu Leu Ile Asn Asp Lys Val Ala Gln Leu Pro
            290                 295                 300 ctg ttt gtc agc gat ggc aag tgg cac cat atc tgc atc acc tgg acc   1081
Leu Phe Val Ser Asp Gly Lys Trp His His Ile Cys Ile Thr Trp Thr
        305                 310                 315 act cga gac ggc atg tgg gaa gca ttc cag gac ggg gag aag ctg ggc   1129
Thr Arg Asp Gly Met Trp Glu Ala Phe Gln Asp Gly Glu Lys Leu Gly
    320                 325                 330 acc ggg gag aac ctg gca ccc tgg cat ccc atc aag cca ggg ggt gtg   1177
Thr Gly Glu Asn Leu Ala Pro Trp His Pro Ile Lys Pro Gly Gly Val
335                 340                 345                 350 ctc atc ctg ggg cag gag cag gac act gtg gga ggc aga ttt gat gcc   1225
Leu Ile Leu Gly Gln Glu Gln Asp Thr Val Gly Gly Arg Phe Asp Ala
                355                 360                 365 aca cag gcc ttc gtt gga gag ctt agc cag ttc aac ata tgg gac cgt   1273
Thr Gln Ala Phe Val Gly Glu Leu Ser Gln Phe Asn Ile Trp Asp Arg
            370                 375                 380 gtc ctc cgg gca caa gag atc atc aac atc gcc aac tgc tcc acg aac   1321
Val Leu Arg Ala Gln Glu Ile Ile Asn Ile Ala Asn Cys Ser Thr Asn
        385                 390                 395 atg cct gga aac atc atc cca tgg gtg gac aac aat gtc gat gtg ttt   1369
Met Pro Gly Asn Ile Ile Pro Trp Val Asp Asn Asn Val Asp Val Phe
```

```
                400             405             410
gga ggg gct tcc aag tgg cct gtg gag acg tgc gaa gag cgt ctc ctg    1417
Gly Gly Ala Ser Lys Trp Pro Val Glu Thr Cys Glu Glu Arg Leu Leu
415                 420                 425                 430 gac ttg tagctacctt ctccctgtcc cagaggccaa gagcgggctg ttctggggag     1473
Asp Leu ttcaaggcat ctattcccga gttcaactaa aatctctggc ctgagtagga aagaaccaga  1533
gcccctaagg caggctgtgt ggcctccttt gtcttaggct cctatgttct tactgctttg  1593
ttctttggtg ggaagtgacc gaagccctgg gaagagtcct gagccacttc ctgctggggt  1653
ttctagtaaa gtctgtgagc ctctccaccc ctcctgtaaa tgctagtgca acccagccct  1713
gcctgtcatt ttggatcctt agtgtctcgt gtgtgcttcc cgtctgtccc ctttgatggc  1773
tgtgtggtca tcctaccggg gtggcctggg tcccttgtgt gtgtagcaca tccctgcttt  1833
tgactgaaca cagtgcacag aagctacccg cccctgaaac agggtctctc cctcagtgtc  1893
atgtgcactc tggtctctcc ctctgagggg actgcagctg ctggagggcc agctgcccag  1953 acagtccccca gcatcccaa agcagaccct ccgccatgga gaaagtcccc cacagcttcc  2013
ccaccctctg tccacctctc agaccccacg cttctaagga ccattgctgg gttggctttc  2073
aaaagctgct gctctcatct ggtgccaaaa gttcatttgc agcttctaca ccgttctgtg  2133
tggtttgggg attgacttta ttcccccaca aaagaggaac agccattaga agccagcctc  2193
ccctcctttt gatgctcagc ccactgtgaa gagtgagctt gcttgtaagc cacattggtt  2253
tctgtgagca tctgactctc ccccgtccag tatttccccc ggaactggag attcgagcct  2313
agttcggctg ctacctgctt agtgactcca ggctgcatca tgtatcataa tttatttttaa 2373 agacaaagtg attcagtggg gaaatttata aagctataaa tattatatat tttatttttc  2433
atacatgttt aaagtgcgga tccatggatg ttccatttgt aggaccagct tgacgtgccc  2493
atcctgacat tgtatgccac aagagctctt gtgatgatgg aattttgatt aaagtgcact  2553
ggaagatgaa aaaaaa                                                   2569
```

<210> SEQ ID NO 2
<211> LENGTH: 432
<212> TYPE: PRT
<213> ORGANISM: ARTIFICIAL
<220> FEATURE:
<223> OTHER INFORMATION: Narp cDNA

<400> SEQUENCE: 2

```
Met Leu Ala Leu Leu Thr Ala Gly Val Ala Leu Ala Val Ala Ala Gly
1               5                   10                  15

Gln Ala Gln Asp Asn Pro Ile Pro Gly Ser Arg Phe Val Cys Thr Ala
                20                  25                  30

Leu Pro Pro Glu Ala Ala Arg Ala Gly Cys Pro Leu Pro Ala Met Pro
            35                  40                  45

Met Gln Gly Gly Ala Leu Ser Pro Glu Glu Leu Arg Ala Ala Val
        50                  55                  60

Leu His Trp Arg Glu Thr Val Val Gln Gln Lys Glu Thr Leu Gly Ala
65                  70                  75                  80

Gln Arg Glu Ala Ile Arg Glu Leu Thr Ser Lys Leu Ala Arg Cys Glu
                85                  90                  95

Gly Leu Ala Gly Gly Lys Ala Arg Gly Thr Gly Ala Thr Gly Lys Asp
            100                 105                 110

Thr Met Gly Asp Leu Pro Arg Asp Pro Gly His Val Val Glu Gln Leu
```

|   |   |   | 115 |   |   |   | 120 |   |   |   | 125 |   |
|---|---|---|---|---|---|---|---|---|---|---|---|---|

Ser Arg Ser Leu Gln Thr Leu Lys Asp Arg Leu Glu Ser Leu Glu Leu
130 135 140

Gln Leu His Thr Asn Ala Ser Asn Ala Gly Leu Pro Ser Asp Phe Arg
145 150 155 160

Glu Val Leu Gln Arg Arg Leu Gly Glu Leu Glu Arg Gln Leu Leu Arg
165 170 175

Lys Val Ala Glu Leu Glu Asp Glu Lys Ser Leu Leu His Asn Glu Thr
180 185 190

Ser Ala His Arg Gln Lys Thr Glu Asn Thr Leu Asn Ala Leu Leu Gln
195 200 205

Arg Val Thr Glu Leu Glu Arg Gly Asn Ser Ala Phe Lys Ser Pro Asp
210 215 220

Ala Phe Lys Val Ser Leu Pro Leu Arg Thr Asn Tyr Leu Tyr Gly Lys
225 230 235 240

Ile Lys Lys Thr Leu Pro Glu Leu Tyr Ala Phe Thr Ile Cys Leu Trp
245 250 255

Leu Arg Ser Ser Ala Ser Pro Gly Ile Gly Thr Pro Phe Ser Tyr Ala
260 265 270

Val Pro Gly Gln Ala Asn Glu Ile Val Leu Ile Glu Trp Gly Asn Asn
275 280 285

Pro Ile Glu Leu Leu Ile Asn Asp Lys Val Ala Gln Leu Pro Leu Phe
290 295 300

Val Ser Asp Gly Lys Trp His His Ile Cys Ile Thr Trp Thr Thr Arg
305 310 315 320

Asp Gly Met Trp Glu Ala Phe Gln Asp Gly Glu Lys Leu Gly Thr Gly
325 330 335

Glu Asn Leu Ala Pro Trp His Pro Ile Lys Pro Gly Gly Val Leu Ile
340 345 350

Leu Gly Gln Glu Gln Asp Thr Val Gly Gly Arg Phe Asp Ala Thr Gln
355 360 365

Ala Phe Val Gly Glu Leu Ser Gln Phe Asn Ile Trp Asp Arg Val Leu
370 375 380

Arg Ala Gln Glu Ile Ile Asn Ile Ala Asn Cys Ser Thr Asn Met Pro
385 390 395 400

Gly Asn Ile Ile Pro Trp Val Asp Asn Val Asp Val Phe Gly Gly
405 410 415

Ala Ser Lys Trp Pro Val Glu Thr Cys Glu Glu Arg Leu Leu Asp Leu
420 425 430

<210> SEQ ID NO 3
<211> LENGTH: 208
<212> TYPE: PRT
<213> ORGANISM: ARTIFICIAL
<220> FEATURE:
<223> OTHER INFORMATION: RAT SAP

<400> SEQUENCE: 3

Gln Thr Asp Leu Asn Gln Lys Val Phe Val Phe Pro Arg Glu Ser Glu
1 5 10 15

Thr Asp Tyr Val Lys Leu Ile Pro Trp Leu Glu Lys Pro Leu Gln Asn
20 25 30

Phe Thr Leu Cys Phe Arg Ala Tyr Ser Asp Leu Ser Arg Ser Gln Ser
35 40 45

Leu Phe Ser Tyr Ser Val Asn Ser Arg Asp Asn Glu Leu Leu Ile Tyr

-continued

```
            50                  55                  60
Lys Ala Lys Leu Glu Gln Tyr Ser Leu Tyr Ile Gly Asn Ser Lys Val
 65                  70                  75                  80

Thr Val Arg Gly Leu Glu Glu Phe Pro Ser Pro Ile His Phe Cys Thr
                 85                  90                  95

Ser Trp Glu Ser Ser Ser Gly Ile Ala Glu Phe Trp Val Asn Gly Lys
                100                 105                 110

Pro Trp Val Lys Lys Gly Leu Gln Lys Gly Tyr Thr Val Lys Ser Ser
                115                 120                 125

Pro Ser Ile Val Leu Gly Gln Glu Gln Asp Thr Tyr Gly Gly Gly Phe
            130                 135                 140

Asp Lys Thr Gln Ser Phe Val Gly Glu Ile Ala Asp Leu Tyr Met Trp
145                 150                 155                 160

Asp Ser Val Leu Thr Pro Glu Asn Ile His Ser Val Asp Arg Gly Phe
                165                 170                 175

Pro Pro Asn Pro Asn Ile Leu Asp Trp Arg Ala Leu Asn Tyr Glu Ile
                180                 185                 190

Asn Gly Tyr Val Val Ile Lys Pro Arg Met Trp Asp Asn Lys Ser Ser
            195                 200                 205
```

<210> SEQ ID NO 4
<211> LENGTH: 211
<212> TYPE: PRT
<213> ORGANISM: ARTIFICIAL
<220> FEATURE:
<223> OTHER INFORMATION: RAT CRP

<400> SEQUENCE: 4

```
His Glu Asp Met Ser Lys Gln Ala Phe Val Phe Pro Gly Val Ser Ala
  1               5                  10                  15

Thr Ala Tyr Val Ser Leu Glu Ala Glu Ser Lys Lys Pro Leu Glu Ala
                 20                  25                  30

Phe Thr Val Cys Leu Tyr Ala His Ala Asp Val Ser Arg Ser Phe Ser
                 35                  40                  45

Ile Phe Ser Tyr Ala Thr Lys Thr Ser Phe Asn Glu Ile Leu Leu Phe
             50                  55                  60

Trp Thr Arg Gly Gln Gly Phe Ser Ile Ala Val Gly Gly Pro Glu Ile
 65                  70                  75                  80

Leu Phe Ser Ala Ser Glu Ile Pro Glu Val Pro Thr His Ile Cys Ala
                 85                  90                  95

Thr Trp Glu Ser Ala Thr Gly Ile Val Glu Leu Trp Leu Asp Gly Lys
                100                 105                 110

Pro Arg Val Arg Lys Ser Leu Gln Lys Gly Tyr Ile Val Gly Thr Asn
            115                 120                 125

Ala Ser Ile Ile Leu Gly Gln Glu Gln Asp Ser Tyr Gly Gly Gly Phe
            130                 135                 140

Asp Ala Asn Gln Ser Leu Val Gly Asp Ile Gly Asp Val Asn Met Trp
145                 150                 155                 160

Asp Phe Val Leu Ser Pro Glu Gln Ile Asn Ala Val Tyr Val Gly Arg
                165                 170                 175

Val Phe Ser Pro Asn Val Leu Asn Trp Arg Ala Leu Lys Tyr Glu Thr
            180                 185                 190

His Gly Asp Val Phe Ile Lys Pro Gln Leu Trp Pro Leu Thr Asp Cys
            195                 200                 205

Cys Glu Ser
```

-continued

```
        210

<210> SEQ ID NO 5
<211> LENGTH: 232
<212> TYPE: PRT
<213> ORGANISM: ARTIFICIAL
<220> FEATURE:
<223> OTHER INFORMATION: RAT NARP

<400> SEQUENCE: 5

Asn Thr Leu Asn Ala Leu Leu Gln Arg Val Thr Glu Leu Glu Arg Gly
1               5                   10                  15

Asn Ser Ala Phe Lys Ser Pro Asp Ala Phe Lys Val Ser Leu Pro Leu
            20                  25                  30

Arg Thr Asn Tyr Leu Tyr Gly Lys Ile Lys Lys Thr Leu Pro Glu Leu
        35                  40                  45

Tyr Ala Phe Thr Ile Cys Leu Trp Leu Arg Ser Ser Ala Ser Pro Gly
50                  55                  60

Ile Gly Thr Pro Phe Ser Tyr Ala Val Pro Gly Gln Ala Asn Glu Ile
65                  70                  75                  80

Val Leu Ile Glu Trp Gly Asn Asn Pro Ile Glu Leu Leu Ile Asn Asp
                85                  90                  95

Lys Val Ala Gln Leu Pro Leu Phe Val Ser Asp Gly Lys Trp His His
            100                 105                 110

Ile Cys Ile Thr Trp Thr Thr Arg Asp Gly Met Trp Glu Ala Phe Gln
        115                 120                 125

Asp Gly Glu Lys Leu Gly Thr Gly Glu Asn Leu Ala Pro Trp His Pro
130                 135                 140

Ile Lys Pro Gly Gly Val Leu Ile Leu Gly Gln Gln Asp Thr Val
145                 150                 155                 160

Gly Gly Arg Phe Asp Ala Thr Gln Ala Phe Val Gly Glu Leu Ser Gln
                165                 170                 175

Phe Asn Ile Trp Asp Arg Val Leu Arg Ala Gln Glu Ile Ile Asn Ile
            180                 185                 190

Ala Asn Cys Ser Thr Asn Met Pro Gly Asn Ile Ile Pro Trp Val Asp
        195                 200                 205

Asn Asn Val Asp Val Phe Gly Gly Ala Ser Lys Trp Pro Val Glu Thr
    210                 215                 220

Cys Glu Glu Arg Leu Leu Asp Leu
225                 230

<210> SEQ ID NO 6
<211> LENGTH: 426
<212> TYPE: PRT
<213> ORGANISM: ARTIFICIAL
<220> FEATURE:
<223> OTHER INFORMATION: APEXIN

<400> SEQUENCE: 6

Met Leu Ala Leu Leu Ala Ala Gly Val Ala Phe Ala Val Val Val Leu
1               5                   10                  15

Ala Gln Asp Lys Pro Leu Pro Gly Ser His Phe Val Cys Ser Ala Ile
            20                  25                  30

Pro Pro Glu Ala Leu Phe Ala Gly Cys Pro Leu Pro Ala Thr Pro Met
        35                  40                  45

Gln Gly Val Ser Leu Ser Pro Glu Glu Glu Leu Arg Ala Ala Val Leu
50                  55                  60
```

-continued

Gln Leu Arg Glu Thr Val Val Met Gln Lys Glu Thr Leu Gly Ala Gln
65                  70                  75                  80

Phe Ser Ala Ile Arg Glu Leu Thr Ser Lys Leu Ala Arg Cys Glu Gly
                85                  90                  95

Leu Met Ala Gly Lys Ala Glu Ser Ser Lys Asp Thr Met Gly Asp Leu
            100                 105                 110

Pro Arg Asp Pro Ser Arg Val Val Glu Gln Leu Ser Arg Ser Leu Gln
        115                 120                 125

Val Leu Lys Asp Arg Leu Glu Ser Leu Glu Leu Arg Thr Asn Ala Ser
130                 135                 140

Asn Thr Gly Leu Pro Ser Asp Phe Arg Glu Val Leu Gln Arg Arg Leu
145                 150                 155                 160

Gly Glu Leu Glu Arg Gln Leu Leu Arg Lys Val Ala Glu Leu Glu Asp
                165                 170                 175

Glu Lys Ser Leu Leu His Asn Glu Thr Ser Ala His Gln Gln Lys Thr
            180                 185                 190

Ser Asn Thr Leu Asn Ala Leu Leu Gln Arg Val Thr Glu Leu Glu Arg
        195                 200                 205

Gly Asn Ser Ala Phe Lys Ser Pro Asp Ala Phe Lys Val Ser Leu Pro
210                 215                 220

Arg Arg Thr Asn Tyr Leu Tyr Gly Lys Ile Lys Lys Thr Leu Pro Glu
225                 230                 235                 240

Leu Tyr Ser Phe Thr Ile Cys Leu Trp Leu Arg Ser Ser Ala Ser Pro
                245                 250                 255

Gly Ile Gly Thr Pro Phe Ser Tyr Ala Val Pro Gly Gln Ala Asn Glu
            260                 265                 270

Ile Val Leu Ile Glu Trp Gly Asn Asn Pro Ile Glu Leu Leu Ile Asn
        275                 280                 285

Asp Lys Val Ala Gln Leu Pro Leu Phe Val Ser Asp Gly Lys Trp His
290                 295                 300

His Ile Cys Ile Thr Trp Thr Thr Arg Asp Gly Leu Trp Glu Ala Phe
305                 310                 315                 320

Gln Asp Gly Glu Lys Leu Gly Thr Gly Glu Asn Leu Ala Pro Trp His
                325                 330                 335

Pro Ile Lys Ser Gly Gly Val Pro Leu Ile Leu Gly Gln Glu Gln Asp
            340                 345                 350

Thr Val Gly Gly Arg Phe Asp Ala Thr Gln Ala Phe Val Gly Glu Leu
        355                 360                 365

Ser Gln Phe Asn Ile Trp Asp Arg Val Leu Arg Pro Gln Glu Asp Ser
370                 375                 380

Asn Ile Ala Asn Cys Ser Leu Asn Met Ala Gly Asn Ile Ile Pro Trp
385                 390                 395                 400

Val Glu Asn Asn Val Asp Val Phe Gly Gly Ala Ser Lys Trp Phe Val
                405                 410                 415

Glu Thr Asp Glu Glu Arg Leu Leu Asp Leu
            420                 425

<210> SEQ ID NO 7
<211> LENGTH: 430
<212> TYPE: PRT
<213> ORGANISM: ARTIFICIAL
<220> FEATURE:
<223> OTHER INFORMATION: NPTXT

<400> SEQUENCE: 7

-continued

```
Met Leu Ala Leu Leu Ala Ala Ser Val Ala Leu Ala Val Ala Ala Gly
1               5                   10                  15

Ala Gln Asp Ser Pro Ala Pro Gly Ser Arg Phe Val Cys Thr Ala Leu
            20                  25                  30

Pro Pro Glu Ala Val His Ala Gly Cys Pro Leu Pro Ala Met Pro Met
        35                  40                  45

Gln Gly Gly Ala Gln Ser Pro Glu Glu Leu Arg Ala Ala Val Leu
    50                  55                  60

Gln Leu Arg Glu Thr Val Val Gln Gln Lys Glu Thr Leu Ala Ser Ala
65                  70                  75                  80

Arg Ala Ile Arg Glu Leu Thr Gly Lys Leu Ala Arg Cys Glu Gly Leu
                85                  90                  95

Ala Gly Gly Lys Ala Arg Gly Ala Gly Ala Thr Gly Lys Asp Thr Met
            100                 105                 110

Gly Asp Leu Pro Arg Asp Pro Gly His Val Val Glu Gln Leu Ser Arg
            115                 120                 125

Ser Leu Gln Thr Leu Lys Asp Arg Leu Glu Ser Leu Glu His Gln Leu
        130                 135                 140

Arg Ala Asn Val Ser Asn Ala Gly Leu Pro Gly Asp Phe Arg Glu Val
145                 150                 155                 160

Leu Gln Gln Arg Leu Gly Glu Leu Glu Arg Gln Leu Leu Arg Lys Val
                165                 170                 175

Ala Glu Leu Glu Asp Glu Lys Ser Leu Leu His Asn Glu Thr Ser Ala
            180                 185                 190

His Arg Gln Lys Thr Glu Ser Thr Leu Asn Ala Ala Leu Gln Arg Val
        195                 200                 205

Thr Glu Leu Glu Arg Gly Asn Ser Ala Phe Lys Ser Pro Asp Ala Phe
    210                 215                 220

Lys Val Ser Leu Pro Leu Arg Thr Asn Tyr Leu Tyr Gly Lys Ile Lys
225                 230                 235                 240

Lys Thr Leu Pro Glu Leu Tyr Ala Phe Thr Ile Cys Leu Trp Leu Arg
                245                 250                 255

Ser Ser Ala Ser Pro Gly Ile Gly Thr Pro Phe Ser Tyr Ala Val Pro
            260                 265                 270

Gly Gln Ala Asn Glu Ile Leu Leu Ile Glu Trp Gly Asn Asn Pro Ile
        275                 280                 285

Glu Leu Leu Ile Asn Asp Lys Val Ala Gln Leu Pro Leu Phe Val Ser
    290                 295                 300

Asp Gly Lys Trp His His Ile Cys Val Thr Trp Thr Thr Arg Asp Gly
305                 310                 315                 320

Met Trp Glu Ala Phe Gln Asp Gly Glu Lys Leu Gly Thr Gly Glu Asn
                325                 330                 335

Leu Ala Pro Trp His Pro Ile Asn Pro Gly Gly Val Leu Ile Leu Gly
            340                 345                 350

Gln Glu Gln Asp Thr Val Gly Gly Arg Phe Asp Ala Thr Gln Ala Phe
        355                 360                 365

Val Gly Glu Leu Ser Gln Phe Asn Ile Trp Asp Pro Val Leu Phe Ala
    370                 375                 380

Gln Glu Ile Val Asn Ile Ala Asn Cys Ser Thr Asn Met Pro Gly Asn
385                 390                 395                 400

Ile Ile Pro Trp Val Ser Asn Asn Val Asp Val Phe Gly Gly Ala Ser
                405                 410                 415

Lys Trp Pro Val Glu Thr Cys Glu Glu Ala Leu Leu Asp Leu
```

```
<210> SEQ ID NO 8
<211> LENGTH: 8
<212> TYPE: PRT
<213> ORGANISM: ARTIFICIAL
<220> FEATURE:
<223> OTHER INFORMATION: "PENTRAXIN FAMILY SIGNATURE" SEQUENCE
<221> NAME/KEY: UNSURE
<222> LOCATION: (1)..(8)
<223> OTHER INFORMATION: X  AT RESIDUES 2,4,7 ARE FOR ANY AMINO ACID
<221> NAME/KEY: VARIANT
<222> LOCATION: (1)..(8)
<223> OTHER INFORMATION: RESIDUES 5 & 8 ARE EITHER SERINE OR THREONINE

<400> SEQUENCE: 8

His Xaa Cys Xaa Xaa Trp Xaa Xaa
1               5
```